United States Patent [19]

Mandeville, III et al.

[11] Patent Number: 5,702,696

[45] Date of Patent: *Dec. 30, 1997

[54] IRON-BINDING POLYMERS FOR ORAL ADMINISTRATION

[75] Inventors: W. Harry Mandeville, III, Lynnfield; Stephen Randall Holmes-Farley, Arlington, both of Mass.

[73] Assignee: GelTex Pharmaceuticals, Waltham, Mass.

[*] Notice: The term of this patent shall not extend beyond the expiration date of Pat. No. 5,487,888.

[21] Appl. No.: 567,933

[22] Filed: Dec. 6, 1995

Related U.S. Application Data

[63] Continuation-in-part of Ser. No. 65,546, May 20, 1993, Pat. No. 5,487,888.

[51] Int. Cl.$^6$ .................................................. A61K 31/785
[52] U.S. Cl. ............................ 424/78.12; 424/78.18; 424/78.26
[58] Field of Search ........................... 424/78.1, 78.01, 424/78.12, 78.37, 78.18, 78.26

[56] References Cited

U.S. PATENT DOCUMENTS

| | | | |
|---|---|---|---|
| 3,308,020 | 3/1967 | Wolf et al. | 167/65 |
| 3,803,237 | 4/1974 | Lednicer et al. | 260/584 R |
| 4,504,640 | 3/1985 | Harada et al. | 526/193 |
| 4,528,347 | 7/1985 | Harada et al. | 526/219 |
| 4,540,760 | 9/1985 | Harada et al. | 526/211 |
| 4,605,701 | 8/1986 | Harada et al. | 525/107 |
| 4,625,577 | 12/1986 | Harada et al. | 525/369 |
| 4,777,042 | 10/1988 | Toda et al. | 424/79 |
| 5,114,709 | 5/1992 | St. Pierre et al. | 424/78.12 |
| 5,141,966 | 8/1992 | Porath | 521/32 |
| 5,236,701 | 8/1993 | St. Pierre et al. | 424/78.12 |

FOREIGN PATENT DOCUMENTS

| | | |
|---|---|---|
| 0 162 388 | 11/1985 | European Pat. Off. . |
| 0 459 632 | 12/1991 | European Pat. Off. . |
| 865836 | 4/1961 | United Kingdom . |
| 2 090 605 | 7/1982 | United Kingdom . |
| WO 94/27620 | 12/1994 | WIPO . |
| WO 94/27621 | 12/1994 | WIPO . |
| WO 95/05184 | 2/1995 | WIPO . |
| WO 95/34585 | 12/1995 | WIPO . |

OTHER PUBLICATIONS

Bhaduri, S. et al., "3-Methylenepentane-2,4-dionated Polystyrene as Polydentate Ligand for Transition Metal Ions," *J. Indian Chem. Soc.* A19:362-363 (1980).

Bottino, F. A. et al., "Metla Selectivity Properties of Polymeric Schiff Bases," *Inorg. Nucl. Chem. Letters* 16:417-421 (1980).

Furue et al., "Preparation of Poly(vinyl-2,2'-Bipyridine) and Complex Formation with Various Metal Ions," *J. of Polymer Science: Polymer Letters Edition*, 20:291-295 (1982).

Ghosh et al., "Preparation and Properties of a new Chelating Resin Containing 1-nitroso-2-naphthol as the Functional Group," *Talanta*, 28:274-276 (1981).

Hodgkin, J. B. et al., "Use of $^{13}$C-NMR in the Study of Reactions on Crosslinked Resins," *J. Of Polymer Science*, 19:1239-1249 (1981).

Lee, C. et al., "The Use of a Chelating Resin Column for Preconcentrated of Trace Elements from Sea-Water in their Determination by Neutron-Activation Analysis," *Talanta*, 24:241-245 (1977).

Melby, L. R. et al., "Polymers for Selective Chelation of Transition Metal Ions," *J. of Am. Chem. Society*, 97:4045-4051 (1975).

Patel, H. S. and Patel S. R., "Preparation and Chelating Properties of 4-Bromosalicyclic Acid-Formaldehyde Polymers," *J. Macromol. Sci. Chem.*, A17(9):1383-1398 (1982).

Warshawsky, A. et al., "Functionalization of Polystyrene. 1. Alkylation with Substituted Benzyl Halide and Benzyl Halide Alcohol Compounds," *J. Org. Chem.*, 43(16)3151-3157 (1978).

Warshawsky, A. et al. "Polymeric Pseudocrown Ethers. 1. Synthesis and Complexation with Transition Metal Anions," *J. Of Am. Chem. Society*, 101:4249-4258 (1979).

Warshawsky, A. "Chelating ion Exchangers" Ion Exchange and Sorption Processes in Hydrometallurgy Critical Reports on Applied Chemistry, J. Wiley & Sons 15:166-266 (1987).

Winston, A. and Kirchner D., "Hydroxamic Acid Polymers. Effect of Structure on the Selective Chelation of Iron in Water," *Hydroxamic Acid Polymers*, 11(3):597-603 (1978).

Winston, A., "Hydroxamic Acid Polymers. II. Design of a Polymeric Chelating Agent for Ion," *J. of Polymer Science*, 14:2155-2165 (1976).

Edwards C. Q., and Kushner, J. P., "Screening for Hemochromatosis" *The New England Journal of Medicine*, 328:1616-1620 (Jun. 1983).

Winston, A. et al., "Functional Polymers for Removal of Heavy-Metal Pollutants from Water," Water Research Inst. Technical Project A-031-WVA (1980).

*Primary Examiner*—Edward J. Webman
*Attorney, Agent, or Firm*—Hamilton, Brook, Smith & Reynolds, P.C.

[57] ABSTRACT

Iron binding polymers are provided for decreasing the absorption of iron from the gastrointestinal tract. The polymers are orally administered, and are useful for treatment of iron overload disorders.

35 Claims, No Drawings

IRON-BINDING POLYMERS FOR ORAL ADMINISTRATION

RELATED APPLICATION

This application is a Continuation-in-Part of Ser. No. 08/065,546 filed May 20, 1993, now U.S. Pat. No. 5,487,888, the entire teachings of which are incorporated herein by reference.

BACKGROUND OF THE INVENTION

This invention relates to iron-binding polymers, particularly polymers administered orally to decrease the absorption of dietary iron from the gastrointestinal tract.

Reduced uptake of dietary iron is clinically important in several related metabolic disorders. In patients with hemochromatosis too much dietary iron is absorbed and patients experience iron overload. Genetic hemochromatosis is due to a somatic gene mutation. While tissue damage is greatest in individuals who are homozygous for the defective gene, reduction of iron uptake is also desirable in patients who are heterozygous for the implicated mutation (Finch et al., *N. Engl. J. Med.*, 306:1520 (1982)). Acquired hemochromatosis includes conditions characterized by tissue injury associated with iron overload, where disease processes other than genetic mutations cause the exacerbated iron uptake. Examples of such diseases include iron-loading anemias, such as thalassemia and sideroblastic anemia, as well as certain types of liver dysfunction (Finch et al., *N. Engl. J. Med.*, 306:1520 (1982)). The massive deposits of iron in body tissues cause similar organ failure in both genetic and acquired hemochromatosis.

Until recently, relatively high iron levels were considered desirable in all individuals. However, increased rates of heart disease are now known to be associated with elevated serum ferritin levels (an indicator of the body burden of iron). In the heterozygous state of hemochromatosis, for example, the degree of iron overload is not sufficient to lead to the traditional symptoms of overload, including abdominal pain, hepatomegaly, diabetes, impotence, and gray pigmentation of the skin. The iron overload may be sufficient, however, to lead to increased probability of heart disease such as congestive heart failure.

A typical adult man has 4–6 g of iron in his body, and absorbs approximately 1 mg of the 10–20 mg of iron available from his daily diet. Iron is absorbed in two basic forms, free iron and heme-bound iron. Free iron can be in either the Ferrous ($Fe^{+2}$) or ferric ($Fe^{+3}$) forms, and can be complexed to various organic and inorganic dietary ingredients (such as phosphate, phytase and citrate). The two forms of free iron are absorbed equally well provided that they both remain in an ionized form, and not in the easily formed and insoluble hydroxides. A typical adult diet contains approximately 1.6 mg of heme-bound iron and 13 mg of free iron. Heme-bound iron,while present in smaller amounts in the diet than free iron, is more readily absorbed than free iron. Approximately 23% of heme-bound iron is available for absorption, while the absorbable fraction of dietary free iron ranges from 3–8%, depending on the other constituents of the diet. The result of these factors is that both heme-bound and free iron contribute significantly to dietary iron uptake.

Iron is absorbed primarily in the proximal segments of the small intestine. It is absorbed by the mucosal cells, processed into appropriate forms, and released into the plasma.

SUMMARY OF THE INVENTION

In general, the invention features a method of reducing dietary iron absorption in a patient which involves oral administration of a therapeutically effective amount of one or more iron-binding polymers that are non-toxic and stable once ingested.

By "non-toxic" it is meant that when ingested in therapeutically effective amounts neither the polymers nor any ions released into the body upon ion exchange are harmful.

By "stable" it is meant that when ingested in therapeutically effective amounts the polymers do not dissolve or otherwise decompose to form potentially harmful by-products, and remain substantially intact so that they can transport bound iron out of the body.

By "salt" it is meant that the nitrogen group in the repeat unit is protonated to create a positively charged nitrogen atom associated with a negatively charged counterion.

By "alkylating agent" it is meant a reactant which, when reacted with the polymer, causes an alkyl group or derivative thereof (e.g., a substituted alkyl, such as an aralkyl, hydroxyalkyl, alkylammonium salt, alkylamide, or combination thereof) to be covalently bound to one or more of the nitrogen atoms of the polymer.

In one preferred embodiment the polymer includes primary, secondary, tertiary, or quaternary amines. These amines may include $-NR_3^+$, where each R group, independently, is H or a lower alkyl or aryl group.

One example of a preferred polymer is characterized by a repeating unit having the formula

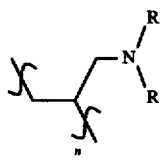

or a copolymer thereof, wherein n is an integer and each R, independently, is H or a substituted or unsubstituted alkyl, alkylamino, or aryl.

A second example of a preferred the polymer is characterized by a repeating unit having the formula

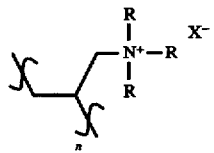

or a copolymer thereof, wherein n is an integer, each R, independently, is H or a substituted or unsubstituted alkyl, alkylamino, or aryl group, and each $X^-$ is an exchangeable negatively charged counterion.

One example of a copolymer according to the second example of the invention is characterized by a first repeating unit having the formula

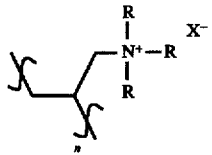

wherein n is an integer, each R, independently, is H or a substituted or unsubstituted alkyl, alkylamino, or aryl group and each X⁻ is an exchangeable negatively charged counterion; and further characterized by a second repeating unit having the formula

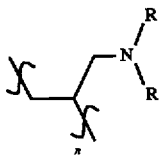

wherein each n, independently, is an integer and each R, independently, is H or a substituted or unsubstituted alkyl, alkylamino, or aryl group.

A fourth example of a preferred polymer is characterized by a repeating unit having the formula

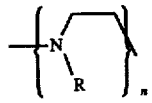

or a copolymer thereof, wherein n is an integer, and R is H or a substituted or unsubstituted alkyl, alkylamino, or aryl group.

One example of a copolymer according to the fourth aspect of the invention is characterized by a first repeating unit having the formula

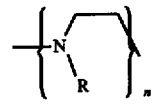

wherein n is an integer, and R is H or a substituted or unsubstituted alkyl, alkylamino or aryl group; and further characterized by a second repeating unit having the formula

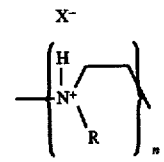

wherein each n, independently, is an integer and R is H or a substituted or unsubstituted alkyl, alkylamino, or aryl group.

A fifth example of a polymer is characterized by a repeating group having the formula

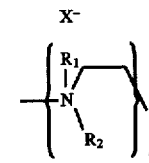

or a copolymer thereof, wherein n is an integer, and each $R_1$ and $R_2$, independently, is H or a substituted or unsubstituted alkyl, alkylamino, or aryl and each X⁻ is an exchangeable negatively charged counterion.

As an example of another preferred polymer, according to the fifth aspect of the invention, at least one of the R groups is a hydrogen atom.

A sixth example of a preferred polymer is characterized by a repeat unit having the formula

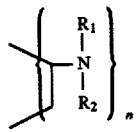

or a copolymer thereof, where n is an integer, each $R_1$ and $R_2$, independently, is H, a substituted or unsubstituted alkyl, alkylamino, or aryl group.

A seventh example of a preferred polymer is characterized by a repeat unit having the formula

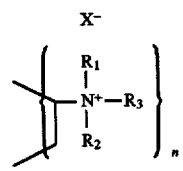

or a copolymer thereof, wherein n is an integer, each $R_1$, $R_2$ and $R_3$, independently, is H, a substituted or unsubstituted alkyl, alkylamino, aryl group and each X⁻ is an exchangeable negatively charged counterion.

An eighth example of a preferred polymer is characterized by one or more crosslinked polymers comprising (1) a hydrophobic co-monomer and
(2) a repeat unit having the formula

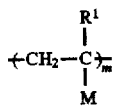

or copolymer thereof, where n is an integer; $R^1$ is H or a $C_1$–$C_{20}$ alkyl group; M is

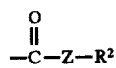

or —Z—$R^2$; Z is O, $NR^3$, S, or $(CH_2)_m$; m=0–10; $R^3$ is H or a $C_1$–$C_{20}$ alkyl group; and $R^2$ is

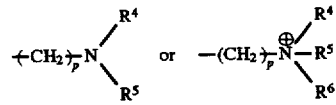

where p=0–10, and each $R^4$, $R^5$, and $R^6$, independently, is H, a $C_1$–$C_{20}$ alkyl group, or an aryl group.

A ninth example of a preferred polymer is characterized by the reaction product of:

(a) one or more crosslinked polymers comprising a repeat unit having the formula:

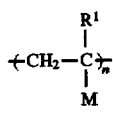

or copolymer thereof, where n is an integer; $R^1$ is H or a $C_1$–$C_{20}$ alkyl group; M is

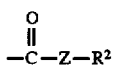

or —Z—R$^2$; Z is O, NR$^3$, S, or (CH$_2$)$_m$; m=0–10; R$^3$ is H or a C$_1$–C$_{20}$ alkyl group; and R$^2$ is

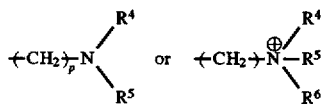

where p=0–10, and each R$^4$, R$^5$, and R$^6$, independently, is H, a C$_1$–C$_{20}$ alkyl group, or an aryl group, alkylated reaction products or copolymers thereof.

A tenth example of a preferred polymer is characterized by the reaction product of:

a) one or more crosslinked polymers characterized by a repeat unit selected from the group consisting of:

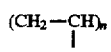

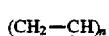

and salts and copolymers thereof, where n is an integer and each R, independently, is H or a C$_1$–C$_{20}$ alkyl group; and b) at least one alkylating agent.

An eleventh example of a preferred polymer is characterized by an amine polymer, comprising:

a) a first substituent, bound to an amine of the amine polymer, that includes a hydrophobic moiety; and b) a second substituent, bound to an amine of the amine polymer, that includes a quaternary amine-containing moiety.

A twelfth example of a preferred polymer is characterized by an amine polymer, comprising a substituent bound to an amine of the amine polymer, the substituent including a quaternary amine-containing moiety having at least one hydrophobic substituent.

The polymers of the invention may be crosslinked.

In another aspect, the invention features a therapeutic composition suitable for oral administration, including a therapeutically effective amount of at least one polymer that binds dietary iron, where the polymer is non-toxic and stable once ingested. By "therapeutically effective" is meant a composition which, when administered to a patient causes decreased absorption of dietary iron.

The invention provides an effective treatment for decreasing the absorption of dietary iron, and thereby reducing the patient's total body iron stores. The compositions are non-toxic and stable when ingested in therapeutically effective amounts.

Other features and advantages will be apparent from the following description of the preferred embodiments and from the claims.

DETAILED DESCRIPTION OF THE INVENTION

The polymers employed in the method described herein have been described by Applicants in copending application Ser. No. 08/065,546, filed May 20, 1993, Ser. No. 08/258,431, filed Jun. 10, 1994, Ser. No. 08/460,980, filed Jun. 5, 1995, Ser. No. 08/461,298, filed Jun. 5, 1995, Ser. No. 08/469,659, filed Jun. 6, 1995, Ser. No. 08/471,747, filed Jun. 6, 1995, Ser. No. 08/471,769, filed Jun. 6, 1995 and Ser. No. 08/482,969, filed Jun. 7, 1995 the contents of which are incorporated herein by reference in their entirety.

The polymers of the invention generally include hydrophilic anion exchange resins, particularly aliphatic amine polymers. The "amine" group can be present in the form of a primary, secondary or tertiary amine, quaternary ammonium salt, amidine, guanadine, hydrazine, or combinations thereof. The amine can be within the linear structure of the polymer (such as in polyethylenimine or a a condensation polymer of a polyaminoalkane, e.g. diethylenetriamine, and a crosslinking agent, such as epichlorohydrin) or as a functional group pendant from the polymer backbone (such as in polyallylamine, polyvinylamine or poly(aminoethyl) acrylate).

In one aspect, the polymer is characterized by a repeating unit having the formula

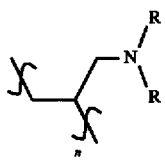

or a copolymer thereof, wherein n is an integer and each R, independently, is H or a substituted or unsubstituted alkyl, such as a lower alkyl (e.g., having between 1 and about 20 carbon atoms), alkylamino (e.g., having between 1 and about 20 carbon atoms, such as ethylamino) or aryl (e.g., phenyl) group.

In another aspect, the polymer is characterized by a repeating unit having the formula

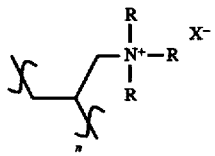

or a copolymer thereof, wherein n is an integer, each R, independently, is H or a substituted or unsubstituted alkyl (e.g., having between 1 and about 20 carbon atoms), alkylamino (e.g., having between 1 and about 20 carbon atoms, such as ethylamino) or aryl (e.g., phenyl) group, and each X$^-$ is an exchangeable negatively charged counterion.

One example of a copolymer of the invention is characterized by a first repeating unit having the formula

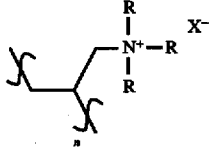

wherein n is an integer, each R, independently, is H or a substituted or unsubstituted alkyl (e.g., having between 1 and about 20 carbon atoms), alkylamino (e.g., having between 1 and about 20 carbon atoms, such as ethylamino)

or aryl group (e.g., phenyl), and each $X^-$ is an exchangeable negatively charged counterion; and further characterized by a second repeating unit having the formula

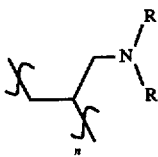

wherein each n, independently, is an integer and each R, independently, is H or a substituted or unsubstituted alkyl (e.g., having between 1 and about 20 carbon atoms), alkylamino (e.g., having between 1 and about 20 carbon atoms, such as ethylamino) or aryl group (e.g., phenyl).

In yet another aspect, the polymer is characterized by a repeating unit having the formula

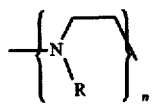

or a copolymer thereof, wherein n is an integer, and R is H or a substituted or unsubstituted alkyl (e.g., having between 1 and about 20 carbon atoms), alkylamino (e.g., having between 1 and about 20 carbon atoms, such as ethylamino) or aryl group (e.g., phenyl).

Another example of a copolymer of the invention is characterized by a first repeating unit having the formula

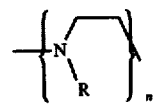

wherein n is an integer, and R is H or a substituted or unsubstituted alkyl (e.g., having between 1 and about 20 carbon atoms), alkylamino (e.g., having between 1 and about 20 carbon atoms such as ethylamino) or aryl group (e.g., phenyl); and further characterized by a second repeating unit having the formula

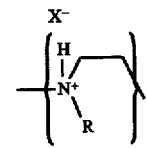

wherein each n, independently, is an integer and R is H or a substituted or unsubstituted alkyl (e.g., having between 1 and about 20 carbon atoms), alkylamino (e.g., having between 1 and about 20 carbon atoms, such as ethylamino) or aryl group (e.g., phenyl).

In still another aspect, the polymer is characterized by a repeating group having the formula

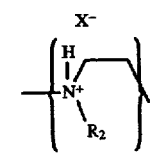

or a copolymer thereof, wherein n is an integer, and each $R_1$ and $R_2$, independently, is H or a substituted or unsubstituted alkyl (e.g., having between 1 and about 20 carbon atoms), and alkylamino (e.g., having between 1 and about 20 carbon atoms, such as ethylamino) or aryl group (e.g., phenyl), and each $X^-$ is an exchangeable negatively charged counterion. A preferred polymer has at least one hydrogen as one of the R groups.

In still another aspect, the polymer is characterized by a repeat unit having the formula

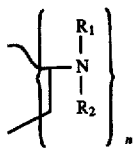

or a copolymer thereof, where n is an integer, each $R_1$ and $R_2$, independently, is H, a substituted or unsubstituted alkyl group containing 1 to about 20 carbon atoms, an alkylamino group (e.g., having between 1 and about 20 carbon atoms, inclusive, such as ethylamino), or an aryl group containing 6 to 20 atoms (e.g., phenyl).

In yet another aspect, the polymer is characterized by a repeat unit having the formula

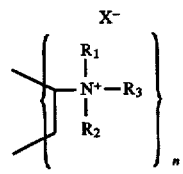

or a copolymer thereof, wherein n is an integer, each $R_1$, $R_2$ and $R_3$, independently, is H, a substituted or unsubstituted alkyl group containing 1 to 20 carbon atoms, an alkylamino group (e.g., having between 1 and about 20 carbon atoms, such as ethylamino), or an aryl group containing 6 to 20 atoms (e.g., phenyl), and each $X^-$ is an exchangeable negatively charged counterion.

In each case, the R groups can carry one or more substituents. Suitable substituents include therapeutic anionic groups, e.g., quaternary ammonium groups, or amine groups, e.g., primary and secondary alkyl or aryl amines. Examples of other suitable substituents include hydroxy, onercapto, alkoxy, carboxamide, sulfonamide, halogen, alkyl, aryl, oxime, hydrazine, guanadine, urea, and carboxylic acid esters, for example.

The present invention also includes reaction products characterized by repeat unit having the formula:

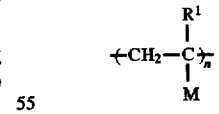

or copolymer thereof, where n is an integer; $R^1$ is H or an alkyl group (which may be straight chain or branched, substituted or unsubstituted, e.g., a $C_1$–$C_{20}$ alkyl, such as methyl); M is

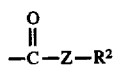

or $-Z-R^2$; Z is O, $NR^3$, S, or $(CH_2)_m$; m=0–10; $R^3$ is H or an alkyl group (which may be straight chain or branched, substituted or unsubstituted, e.g., $C_1$–$C_{20}$ alkyl, such as methyl); and $R^2$ is

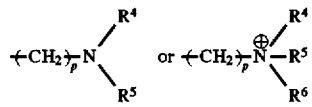

where p=0–10, and each $R^4$, $R^5$, and $R^6$, independently, is H, an alkyl group (which may be straight chain or branched, substituted or unsubstituted, e.g., $C_1$–$C_{20}$ such as methyl), or an aryl group (e.g., having one or more rings and which may be substituted or unsubstituted, e.g., phenyl, naphthyl, imidazolyl, or pryridyl).

Polymers of the invention also include those polymers characterized by the formula:

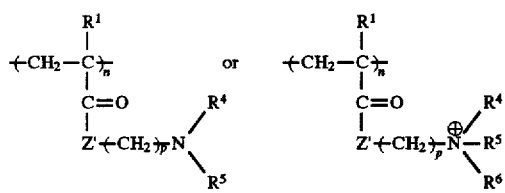

where $R^1$ is hydrogen or methyl, $Z^1$ is O or $NR^3$, $R^3$ is hydrogen or an alkyl group, $R^4$, $R^5$ and $R^6$ are, independently, hydrogen or methyl, and p=2–10.

In a preferred embodiment, the polymer is characterized by the formula:

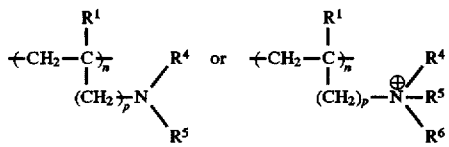

wherein $R^1$ is hydrogen or methyl, $R^4$, $R^5$ and $R^6$ are, independently hydrogen or alkyl and p=0–2.

The polymer can also be characterized by the formula

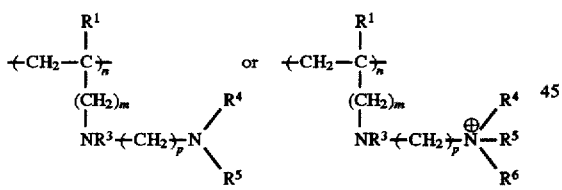

wherein $R^1$ is hydrogen or methyl, $R^3$ is hydrogen or an alkyl group, $R^4$, $R^5$ and $R^6$ are, independently, hydrogen or methyl, and p=2–10.

The polymers also include heteropolymers of two or more of the above.

The polymer further can include one or more hydrophilic or hydrophobic co-monomers, e.g., styrene, vinyl naphthalene, ethyl vinylbenzene, N-alkyl and N-aryl derivatives of acrylamide and methacrylamide, alkyl and aryl acrylates, alkyl and aryl methacrylates, 4-vinylbiphenyl, 4-vinyl-anisole, 4-aminostyrene, and fluorinated derivatives of any of these co-monomers (e.g., p-fluorostyrene, pentafluoro-styrene, hexafluoroisopropylacrylate, hexafluorobutyl-methacrylate, or heptadecafluoro-decylmethacrylate). For example, the co-monomer can be an alkylated derivative or other derivative of one or more of the above mentioned formulae. The alkyl groups are preferably $C_1$–$C_{20}$ (e.g., $C_1$–$C_{20}$ alkyl groups, and may be straight chain, branched, or cyclic (e.g., cyclohexyl), and may further be substituted or unsubstituted. The aryl groups preferably have one or more rings and may be substituted or unsubstituted, e.g., phenyl, naphthyl, imidazolyl, or pyridyl. The polymer may also include one or more positively charged or amine co-monomers, e.g., vinyl pyridine, dimethylaminomethyl styrene, or vinyl imidazole.

Another example of a preferred polymer is characterized by a repeat unit having the formula

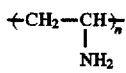

or copolymer thereof. The polymer may further include, as a co-monomer, ethyl vinylbenzene.

In yet another example of a preferred polymer is characterized by a repeat unit having the formula

or copolymer thereof.

In still yet another example of a preferred polymer is characterized by a repeat unit having the formula

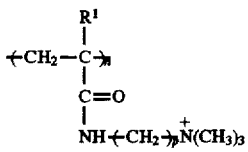

or copolymer thereof. The polymer may also include, as a co-monomer, styrene or a fluorinated derivative thereof.

In another aspect, the invention features polymers and a method for removing iron from a patient by ion exchange that includes administering to the patient a therapeutically effective amount of one or more crosslinked polymers characterized by a repeat unit having the formula

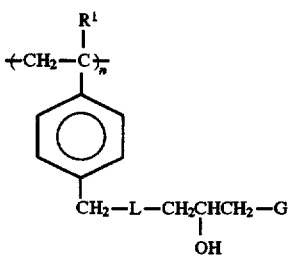

or copolymer thereof, where n is an integer; $R^1$ is H or a $C_1$–$C_{20}$ alkyl group; L is —NH— or

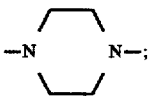

G is

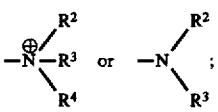

and each $R^2$, $R^3$, and $R^4$, independently, is H, a $C_1$–$C_{20}$ alkyl group, or an aryl group. The polymers are preferably nontoxic and stable once ingested.

One example of a preferred polymer is characterized by a repeat unit having the formula

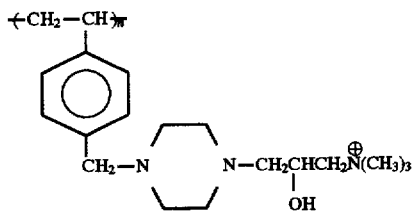

or copolymer thereof. The polymer may further include, as a co-monomer, styrene or a fluorinated derivative thereof.

Another example of a preferred polymer is characterized by a repeat unit having the formula

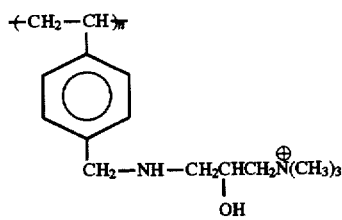

or copolymer thereof.

Optionally, the polymer includes one or more co-monomers that increase the overall hydrophobicity of the polymer. Because iron-heme complexes are hydrophobic, the hydrophobic co-monomer can aid in maximizing the selectivity of the interaction of the polymer with the heme molecule.

Examples of suitable hydrophobic co-monomers include, e.g., acrylamide, methacrylamide, and N-alkyl (e.g., methyl, ethyl, isopropyl, butyl, hexyl, dodecyl, cyclohexyl, dicyclohexyl) and N-aryl (e.g., phenyl, diphenyl) derivatives thereof; alkyl and aryl acrylates and methacrylates (e.g., ethyl, propyl, butyl, dodecyl), and fluorinated derivatives thereof (e.g., hexafluoroisopropyl acrylate, hexafluorobutyl methacrylate, heptadecafluorodecyl acrylate); styrene and derivatives thereof (e.g., dimethylaminomethyl styrene, 4-aminostyrene, and fluorinated derivatives, e.g., p-fluorostyrene, pentafluorosstyrene); ethylvinylbenzene; vinyl napthalene; vinyl pyridine; vinyl imidazole; 4-vinylbiphenyl; 4,4-vinylanisole; and combinations thereof. The amount of co-monomer used in the preparation of these polymers is from 0 to 75% by weight.

The level of hydrophobicity desired can also be achieved simply by appropriate choice of crosslinking co-monomer. For example, divinylbenzene is a suitable crosslinking co-monomer and is hydrophobic as well. In addition, the main "impurity" in divinylbenzene is ethylvinylbenzene, a hydrophobic, polymerizable monomer which will also contribute to the overall hydrophobicity of the polymer. Other hydrophobic crosslinking co-monomers include bisphenol A diacrylate and bisphenol A dimethacrylate.

An additional example of a preferred polymer includes the products of one or more crosslinked polymers having the formulae:

(a) one or more crosslinked polymers characterized by a repeat unit selected from the group consisting of:

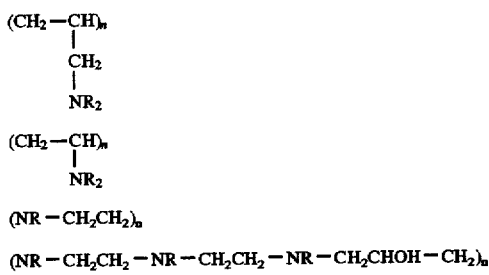

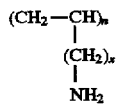

and salts and copolymers thereof, where n is an integer and each R, independently, is H or a substituted or unsubstituted alkyl group (e.g., $C_1$–$C_{20}$ alkyl); and (b) at least one alkylating agent. The reaction product is preferably non-toxic and stable once ingested. The polymers are, in one embodiment, crosslinked. The level of crosslinking makes the polymers completely insoluble and thus limits the activity of the alkylated reaction product to the gastrointestinal tract only. Thus, the compositions are non-systemic in their activity and will lead to reduced side-effects in the patient.

An example of preferred polymer is characterized by a repeat unit having the formula $$(CH_2-CH)_n$$
$$|$$
$$(CH_2)_x$$
$$|$$
$$NH_2$$

or a salt or copolymer thereof; wherein x is zero or an integer between about 1 to 4.

Another example of a preferred polymer is characterized by a repeat unit having the formula $$(NH-CH_2CH_2)_n$$

or a salt or copolymer thereof.

Still yet another example of a preferred polymer is characterized by a repeat unit having the formula $$(NH-CH_2CH_2-NH-CH_2CH_2-NH-CH_2CHOH-CH_2)_n$$

or a salt or copolymer thereof.

The amine polymers of the invention can include distinct first and second substituents. The first substituent is bound to an amine of the amine polymer and can include a hydrophobic moiety. The second substituent is bound to an amine of the amine polymer and includes a quaternary amine-containing moiety. It is to be understood that the first and second substituents can be bound to the same amine and/or different amines of the amine polymer. The amine polymers of the invention are particularly suitable for binding iron in mammals by oral administration of the polymer. A particularly suitable form for oral administration of the amine polymer is that which will form a gel in the stomach of a patient.

Suitable methods by which the amine polymer of the invention can be formed include polymerization of an amine monomer to form a homopolymer. Examples of this method include polymerization of allylamine, ethyleneimine, vinylamine, 1,2-diaminoethene, aminoethylacrylamide, aminopropylacrylate, or p-aminomethylstyrene, to form their respective homopolymers.

Another method involves copolymerizing an amine monomer with one or more additional monomers. These additional monomers include amine monomers, such as those listed above, and non-amine monomers, such as acrylamide, styrene, divinylbenzene, vinyl alcohol, or vinyl chloride. Examples include copoly(allylamine/acrylamide), copoly(vinylamine/allylamine), copoly(aminoethylacrylamide/acrylamide), and copoly(allylamine/divinylbenzene).

Still another method involves polymerization of a non-amine monomer to form a homopolymer that is subsequently chemically modified to form an amino polymer. Examples of this method include polymerization of vinyl formamide, vinyl acetamide, vinyl chloride, vinyl bromide, allyl chloride, allyl bromide, acrylamide, or acrylonitrile, to form their respective homopolymers. Each homopolymer would then be chemically altered to form an amine polymer using such reactions as hydrolysis, nucleophilic substitution, or reduction. The first four homopolymers listed above would then become poly(vinylamine) and the last four would become poly(allylamine). It is to be understood that not all of the initial non-amine monomer need be chemically altered, resulting in an amine polymer that contains some of the initial non-amine monomers in a non-amine state.

Another method involves copolymerizing a non-amine monomer with one or more additional monomers. These additional monomers could include amine monomers and non-amine monomers. The resulting copolymer would then be chemically altered. Examples would include copolymerization of acrylamide and styrene, followed by reduction to form copoly(allylamine/styrene), copolymerization of acrylonitrile and vinyl formamide, followed by reduction and hydrolysis, to form copoly(allylamine/vinylamine), and copolymerization of acrylonitrile and allylamine, followed by reduction, to form poly(allylamine). It is to be understood that not all of the initial non-amine monomer will be therefore chemically altered, resulting in an amine polymer that contains some of the initial non-amine monomers in a non-amine state.

Still another method involves forming an amine polymer through a condensation mechanism. Examples of this method would include reaction of diethylenetriamine and epichlorohydrin, 1,3-dibromopropane and ethylenediamine, spermine and 1,4-butanediol diglycidyl ether, or tris(2-aminoethyl)amine and 1,10-dibromodecane.

Each of these amine polymers typically has a molecular weight greater than 2,000. Examples of resulting suitable amine polymers include poly(vinylamine), poly(allylamine), and poly(ethyleneimine). A preferred amine polymer is poly(allylamine).

The polymers are preferably crosslinked, in some cases by adding a crosslinking co-monomer to the reaction mixture during polymerization. Examples of suitable crosslinking co-monomers are diacrylates and dimethacrylates (e.g., ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate, polyethyleneglycol diacrylate), methylene bisacrylamide, methylene bismethacrylamide, ethylene bisacrylamide, ethylenebismethacrylamide, ethylidene bisacrylamide, divinyl benzene, bisphenol A dimethacrylate, and bisphenol A diacrylate. These crosslinking co-monomers are either commercially available or are prepared as described in Mandeville et al., "Process for Adjusting Ion Concentration in a Patient and Compositions Therefor," U.S. Ser. No. 08/065,113, filed May 20, 1993, assigned to the same assignee as the present application and hereby incorporated by reference.

The amount of crosslinking co-monomer is typically between 1.0 and 25 weight %, based upon combined weight of crosslinking agent and monomer.

In some cases the polymers are crosslinked after polymerization. One method of obtaining such crosslinking involves reaction of the polymer with difunctional crosslinkers, such as epichlorohydrin, succinyl dichloride, the diglycidal ether or bisphenol A, pyromellitic dianhydride, toluene diisocyanate, and ethylenediamine. A typical example is the reaction of poly(ethyleneimine) with epichlorohydrin. In this example the epichlorohydrin (1–100 parts) is added to a solution containing polyethyleneimine (100 parts) and heated to promote reaction. Other methods of inducing crosslinking on already polymerized materials includes, but is not limited to, exposure to ionizing radiation, ultraviolet radiation, electron beams, radicals, and pyrolysis.

Crosslinking of the polymer can be achieved by reacting the polymer with a suitable crosslinking agent in an aqueous caustic solution at about 25° C. for a period of time of about eighteen hours to thereby form a gel. The gel is then combined with water or dried to form a particulate solid. The particulate solid can then be washed with water and dried under suitable conditions, such as a temperature of about 50° C. for a period of time of about eighteen hours.

The amine polymer can be alkylated. One or more alkylating agents can be employed to react with the amine polymer to form substituents on the amine polymer. In one example the first substituent is bound to an amine of the amine polymer, and includes a hydrophobic moiety. Examples of suitable hydrophobic moieties are those which include alkyl groups of at least six carbons. In one embodiment, the hydrophobic moiety includes an alkyl group of between about eight and twelve carbons. Specific examples of suitable hydrophobic moieties include alkyl halides, such as n-hexyl halide, n-ocdodecylide, n-decyl halide, n-dodecyl halide, n-tetradecyl halide, n-octadecyl halide, and combinations thereof. Other examples include: a dihaloalkane that includes an alkyl group of at least six carbons (e.g., a 1,10-dihalodecane); an hydroxyalkyl halide (e.g., an 11-halo-1-undecanol); an aralkyl halide (e.g., a benzyl halide); etc. The alkylating agent can include a suitable leaving group, such as a halide, epoxy, tosylate, or mesylate group. In the case of, e.g., epoxy groups, the alkylation reaction causes opening of the three-membered epoxy ring.

A preferred halogen component of the alkyl halides is bromine. An example of an alkylating agent which, when reacted with the amine polymer, will cause formation of an amine polymer reaction product that includes a first substituent, is 1-bromodecane.

The amine polymer can also be alkylated with a second alkylating agent. The second alkylating agent, when reacted with the amine polymer, will result in an amine polymer reaction product that includes a second substituent that is bound to an amine of the amine polymer. The second substituent can include a quaternary amine-containing moiety. In one embodiment, the quaternary amine-containing moiety of the second substituent includes an alkyl trimethylammonium, wherein the alkyl component includes between about two and twelve carbons. Examples of preferred alkyl groups of the alkyl trimethylammonium are hexyl, octyl, and decyl groups. Examples of suitable second alkylating agents include alkyl halide trimethylammonium salts, such as (4-halobutyl)trimethylammonium salt, (6-halohexyl)trimethylammonium salt, (8-halooctyl) trimethylammonium salt, (10-halodecyl) trimethylammonium salt, (12-halododecyl) trimethylammonium salt, and combinations thereof. A particularly preferred second alkylating agent is (6-bromohexyl)trimethylammonium bromide.

The amine polymer is typically alkylated by combining the polymer with the alkylating agent in a solvent such as an organic solvent or water. Examples of suitable organic solvents include methanol, ethanol, acetonitrile, etc. A preferred organic solvent is methanol.

In another embodiment, the reaction mixture is heated over a period of about forty minutes to a temperature of about 65° C., with stirring. Typically, an aqueous sodium hydroxide solution is intermittently added during the reaction period. Preferably, the reaction period at 65° C. is about eighteen hours, followed by gradual cooling to a room temperature of about 25° C. over a period of about four hours. The resulting reaction product is then filtered, resuspended in methanol, filtered again, and then washed with a suitable aqueous solution, such as two molar sodium chloride, and then with deionized water. The resultant solid product is then dried under suitable conditions, such as at a temperature of about 60° C. in a forced-air oven. The dried solid can then be subsequently processed. Preferably, the solid is ground and passed through an 80 mesh sieve.

In one embodiment of the invention, the amine polymer is a crosslinked poly(allylamine), wherein the substituent includes (3-bromopropyl)dodecyldimethylammonium bromide. Further, the particularly preferred crosslinked poly (allylamine) is crosslinked by epichlorohydrin that is present in a range of between about two and six percent of the amines of the polymer.

In another embodiment, (6-bromohexyl) trimethylammonium bromide can be formed by adding to a 5 L, three-neck flask, equipped with a mechanical stirrer, thermometer, and a condenser at −5° C., tetrahydrofuran (3.0 L) and 1,6-dibromohexane (1.0 kg). To this mixture is added trimethylamine (gas; 241.5 grams) over a 1 hour period. At the end of this addition the temperature is −40° C. The mixture is stirred and temperature maintained at 40° C. for 24 hours. The solid is then filtered off and rinsed with tetrahydrofuran (2.0 L). The solid is dried in a vacuum oven to yield 1070.2 grams of white solid. This solid is then used as an alkylating agent.

In another embodiment of the invention, the amine polymer is a crosslinked poly(allylamine), wherein the first substituent includes a hydrophobic alkyl, such as decyl moiety, and the second amine substituent includes an ammonium substituted alkyl such as hexyltrimethylammonium. Further, the preferred crosslinked poly(allylamine) is crosslinked by epichlorohydrin that is present in a range of between about two and six percent of the amines of the polymer.

The negatively charged counterions, $X^-$, can be organic ions, inorganic ions, or a combination thereof. The inorganic ions suitable for use in this invention include halide (especially chloride), carbonate, bicarbonate, sulfate, bisulfate, hydroxide, nitrate, persulfate and sulfite. Suitable organic ions include acetate, ascorbate, benzoate, citrate, dihydrogen citrate, hydrogen citrate, oxalate, succinate, tartrate, taurocholate, glycocholate, cholate, lactate, propionate, butyrate, ascorbate, maleate, folate, an amino acid derivative, a nucleotide, a lipid, or a phospholipid. The counterions may be the same as, or different from, each other. For example, the polymer may contain two different types of counterions, both of which are exchanged for the iron being removed. More than one polymer, each having different counterions associated with the fixed charges, may be administered as well.

In a preferred embodiment, the counterion does not have a detrimental side effect to the patient but rather is selected to have a therapeutic or nutritional benefit to the patient.

Preferably, the ions released into the body are actually beneficial to the patient. Such is the case when, for example, the exchangeable ions are natural nutrients such as amino acids, or possess a therapeutic value.

The amine polymers of the invention can be subsequently treated or combined with other materials to form compositions for oral administration of amine polymers.

The present pharmaceutical compositions are generally prepared by known procedures using well known and readily available ingredients. In making the compositions of the present invention, the amine polymer can be present alone, can by admixed with a carrier, diluted by a carrier, or enclosed within a carrier which may be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carrier, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc.

The method of the invention includes administering to a mammal, such as by oral administration, a therapeutic amount of the amine polymer having a first substituent, bound to an amine of the amine polymer, that includes a hydrophobic moiety, and a second substituent, bound to an amine of the amine polymer, that includes a quaternary amine-containing moiety. Generally, a therapeutic amount of the amine polymer is an amount of the amine polymer in a range of between about 0.1 grams/day and about 10 grams/day.

Polymers for binding free iron and heme-bound iron may be different, and their efficacies can be assessed by different tests. For these reasons the two types of iron are discussed separately.

Heme-Bound Iron

One method of sequestering heme-bound iron would involve binding it to a polymer, rendering it unable to enter the mucosal cells. The structure of heme-bound iron is shown below.

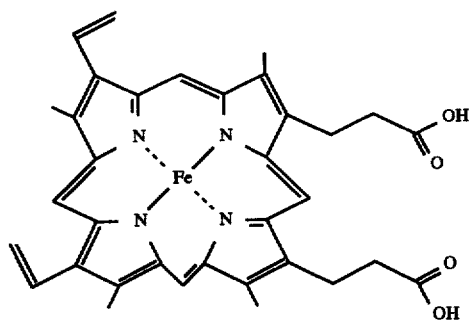

There are several logical ways to attach this molecule to a polymer, as described below.

1. Since in the small intestine the pH would typically be around 7, the two carboxylic acid groups will likely be ionized to form negatively charged $RCO_2^-$ groups. If the polymer contained positively charged groups the heme could be bound by its negatively charged groups through an ion-exchange mechanism. Examples of positively charged groups (at pH 7) would include primary, secondary, tertiary, and quaternary amines.

2. The iron atom itself is also available for binding, even though four of its six sites are taken up by the heme. In natural proteins, such as hemoglobin and cytochrome C, these sites are bound to by such ligands as the nitrogen group of histidine and the sulfur group of methionine. The polymer would thus incorporate one or more appropriate ligands to bind directly to the iron atom.

3. A polymer with a site that provided appropriate solvation for the various parts of the heme-iron would also effectively bind it. The heme unit incorporates a variety of organic functional groups that vary in their solvation requirements, from the various carboxylic acid groups which would be best solvated by polar, hydrogen bonding moieties to the allyl groups which would be better solvated by nonpolar, nonhydrogen-bonding moieties.

4. A preferred embodiment would include a polymer which combined two or more of these mechanisms in a single site or, alternatively, at separate sites.

In order to assess the potential of each candidate polymer a test was devised to quantitate the binding of the iron-heme unit to the polymer. This test involved stirring the polymer in a solution designed to mimic hystiologic conditions. The amount of heme chosen corresponds to 10 mg of iron (a typical daily intake) and is dissolved in 1 L of fluid (the amount typically passing out of the small intestine in one day).

| Heme Iron Test Solution | |
| --- | --- |
| NaCl | 17.5 g |
| NaHCO₃ | 7.6 g |
| Hemin | 0.35 g dissolved in 5 mL 1 M NaOH + 50 mL Water |
| Water | 3 L total volume |
| Acetic Acid | Adjust to pH 7 |

A specified amount of polymer was stirred in 100 mL of this solution for three hours. The pH was adjusted to 7.0 at both the start and end of this period. The solid was then filtered off and the amount of heme still present in the solution was determined spectroscopically. For any given polymer the amount of heme remaining in the solution is a function of the amount of polymer used in the test.

As shown in the following table, the amount of one preferred polymer, poly(ammoniumbutylacrylamide) (ABA), positively correlates with the percent heme remaining after filtration.

| Percent Heme Removed | Polymer Required (g) | Daily Dose (g) |
| --- | --- | --- |
| 50 | 0.05 | 0.5 |
| 75 | 0.07 | 0.7 |
| 90 | 0.11 | 1.1 |
| 99 | 0.13 | 1.3 |
| 99.5 | 0.25 | 2.5 |
| 99.85 | 0.50 | 5.0 |

The daily dose column is an estimate of the dose required by a person who consumes 10 mg/day of heme iron. Thus to sequester 99% of the heme iron from this individual's diet he would have to take 1.3 g of polymer over the course of the day.

This test is extremely sensitive to the pH of the test solution, and care must be made to ensure that the pH is 7.0. As the pH is raised above pH 7, the binding drops off significantly. Further, at pH values below 7 (especially below 5.5) the heme is insoluble and precipitates. Thus the tests must be run carefully at pH 7.

In order to assess the relative binding ability of a variety of polymers, a few selected points were tested. The table below shows the data for a number of such polymers.

| | % Heme Remaining | | | |
| --- | --- | --- | --- | --- |
| Polymer | 0.025 g | 0.05 g | 0.1 g | 0.2 g |
| Poly(ammoniumethylacrylamide) | — | 23 | 0–5.0 | <1 |
| Poly(ammoniumbutylacrylamide) | — | 50 | 19 | 1.3 |
| Poly(ammoniumhexylacrylamide) | — | 43–50 | 10 | 0.3 |
| Poly(dimethylaminopropylacrylamide) | — | 4 | <1 | <1 |
| Poly(dimethylaminopropylacrylamide HCl) | — | 24 | 7 | <1 |
| Poly(ethyleneimine) "A" | 35–50 | 1–36 | <1 | <1 |
| Poly(diethylenetriaminemethacrylamide) | 15–39 | 0–17 | <1 | <1 |
| Poly(diethylaminopropylmethacrylamide) | 5–12 | 0–14 | <1 | <1 |

In order to combine the effects of ion exchange (binding method 1) with those of hydrophobicity (method 3 a series of copolymers was formed. In the first case a copolymer involving ammoniumethylacrylamide (AEA) and allylacrylamide (AA) was made with allylacrylamide portions ranging from 0% to 75%. As can be seen in the data below, the higher the proportion of allylacrylamide in the polymer the poorer the binding is. In this case the added hydrophobicity did not increase the binding.

| Polymer | % Heme Remaining (0.2 g/100 mL) |
| --- | --- |
| 100% AEA | <2 |
| 75% AEA, 25% AA | ~5 |
| 50% AEA, 50% AA | ~35 |
| 25% AEA, 75% AA | ~50 |

Other polymers were also made to test the effects of hydrophobicity on binding. One set includes a comparison of an acrylamide polymer to the more hydrophobic methacrylamide equivalent. A second comparison from this set involves substitution of more hydrophobic ethyl groups for methyl groups. From these comparisons there is no clear trend concerning the effect of hydrophobicity on iron binding effectiveness.

| | % Heme Remaining | | | |
| --- | --- | --- | --- | --- |
| Polymer | 0.025 g | 0.05 g | 0.1 g | 0.2 g |
| Poly(dimethylaminopropylacrylamide) | — | 3 | <1 | <1 |
| Poly(dimethylaminopropylmethacrylamide) | 51 | 32 | <1 | <1 |
| Poly(diethylaminopropylmethacrylamide) | 8 | 2 | <1 | <1 |

Other comparisons involving hydrophobicity come from the following list of polymers:

| Polymer | % Heme Remaining | | |
|---|---|---|---|
| | 0.05 g | 0.1 g | 0.2 g |
| Poly(Ammoniumethylacrylamide) [=Poly(AEA)] | 23 | 0–5 | <1 |
| Copoly(AEA/polyethyleneglycol dimethacrylate) | 59 | 5 | — |
| Poly(Ammoniumhexylacrylamide [=Poly(AHA)] | 43–50 | 10 | 0.3 |
| Copoly(AHA/dodecylacrylamide) | >50 | >50 | ~50 |
| Copoly(AHA/dehydroabeitylacrylamide/ acrylamide) | — | — | >50 |

From these comparisons it is again shown that increased hydrophobicity does not improve iron binding. In order to make many of these comparisons some of the iron binding monomer was diluted with a nonpolar monomer. This dilution necessarily lowers the concentration of the primary monomer. Alternatively one can dilute the primary monomer with a hydrophilic monomer, thereby separating the effects of dilution from those of increased hydrophobicity.

| Polymer | % Heme Remaining | | |
|---|---|---|---|
| | 0.05 g | 0.1 g | 0.2 g |
| Poly(Ammoniumhexylacrylamide [=Poly(AHA)] | 43–50 | 10 | 0.3 |
| Copoly(AHA/hydroxypropylacrylamide) | — | — | >50 |
| Copoly(AHA/acrylamide/vinylphosphonic acid) | >50 | — | >50 |

In this case the iron binding is much worse when the amine functionality is diluted with hydroxyl functionality, a substitution that is not expected to make the polymer significantly more hydrophobic. This result suggests that dilution of the primary monomer is a factor and that hydrophobic/hydrophilic effects may be secondary. Dilution with acrylamide and phosphonic acid functionality also impacts negatively on the binding properties. In this case the negative charge expected on the phosphonic acid groups may inhibit binding of the negatively charged heme groups.

A variety of other amine-containing polymers was tested for heme-iron binding. The data on these polymers is shown below. Clearly the polyvinylamine is very effective (among the best), while the other polymers are less so. It is evident from these and other data that all types of amines (primary, secondary, tertiary, quaternary, and heterocyclic) can be made to bond heme-bound iron.

| Polymer Amine Functionality | % Heme Remaining | | |
|---|---|---|---|
| | 0.05 g | 0.1 g | 0.2 g |
| Polyvinylamine R—NH2 | 4% | <1 | — |
| Poly(N-imidazolepropylacrylamide) $R-N\langle\!\!\langle N$ | 16 | <1 | <1 |
| Poly(aminoethylpiperazine itaconate) $R-CONHCH_2CH_2N(CH_2CH_2)_2NH_2$ or $R-CON(CH_2CH_2)_2NCH_2CH_2NH_2$ | 73 | — | 66 |
| Poly(PEH-acrylamide) $R-NH_2; R-NH-R$ | 78 | 72 | 59 |
| Poly(TAEA-acrylamide) $R-NH_2; R-NR_2$ | 62 | 72 | 70 |
| Poly(Methacrylamidopropyltrimethyl-ammoniumchloride) $R-N^+(CH_3)_3$ | 57 | 12 | <1 |

A variety of polymers with functional groups designed to bond directly to the iron atom within the heme were tested with the results shown below. Two of these, poly(AEABMP) and poly(AEABPHA), also contained an amine functionality that could be positively charged under the conditions of the iron-binding test. Thus they are capable of both direct binding and binding by ion exchange. Those polymers without this capability (the first six in the table below) were less effective than those two with it.

| Polymer (0.2 g used) | Iron Binding Group(s) | % Heme Remaining |
|---|---|---|
| Poly(cysteinediacrylamide) | R—S—S—R | 92 |
| Poly(mercaptoethylacrylamide) | R—SH | 82 |
| Poly(cystaminediacrylamide) | R—S—S—R | >50 |
| Poly(N,N-methylcyanoethylacrylamide) | R—CN | 92 |
| Poly (IAHH) | R—CONHOH; R—CO₂H | 83 |
| Poly(N-hydroxymethacrylamide) | R—CONHOH | 25 |
| Poly (AEABMP) | several | 10 |
| Poly (AEABPHA) | several | <1 |

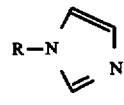

It might be expected that the extent of crosslinking could impact the heme-binding characteristics of these polymers. Since heme is a relatively large molecule it might have difficulty finding its way into a tightly crosslinked polymer gel. Alternatively, a too loosely crosslinked network might not effectively hold a heme molecule because of the potentially greater loss in entropy in binding to it. A highly crosslinked network might have cavities just large enough for a heme to fit tightly in, just as substrates fit in enzymatic active sites, while a less crosslinked (or even uncrosslinked) polymer may have to wrap itself around a heme with a significant loss in its internal entropy.

In order to partially assess such hypotheses two identical polymers with different amounts of crosslinking were synthesized. Poly(ammoniumbutylacrylamide) was synthesized with either 5% or 10% methylenebisacrylamide as crosslinked. The data below show that little difference was observed. Either there is little effect or extent of crosslinking on heme-iron binding, or the effects take place primarily outside of the range tested.

| Crosslinking | 0.05 g | % Heme Remaining | |
|---|---|---|---|
| % | Polymer | 0.1 g Polymer | 0.2 g Polymer |
| 5 | 42 | 17 | <1 |
| 10 | 50 | 19 | 1.3 |

Two commercially available crosslinked polymeric materials that contain amine functionality are Questran® bile salt binder (cholestyramine; Bristol Laboratories) and Colestid® bile salt binder (colestipol; Upjohn). The structures of these polymers are shown below.

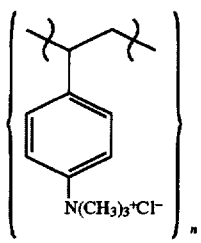

Cholestyramine

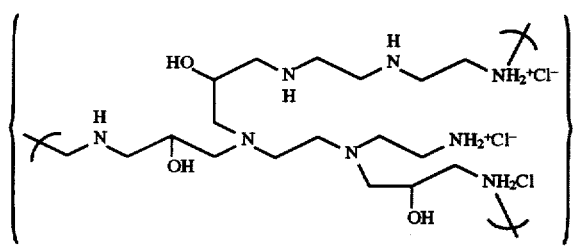

Typical Colestipol Structure

Heme binding test results for these polymers are given in the following table. These products do demonstrate some heme-iron affinity, but they are not as effective as some of the polymers described above.

| Polymer (0.2 g) | % Heme Remaining |
|---|---|
| Cholestyramine | 53 |
| Colestipol | 60 |

Heme iron binding was also tested for two of the polymers in the presence of a variety of potential small intestine contents. A test solution was made up with the following ingredients:

| Ingredient | Amount |
|---|---|
| Hemin | 0.12 g Dissolved in 50 mL water + 3 mL 1 N NaOH |
| Water | To 1 L Total Volume (~900 mL) |
| NaCl | 5.8 g |
| NaHCO$_3$ | 2.5 g |
| Crude Taurocholic Acid | 2.86 g |
| α-Alanine | 0.5 g |
| Arginine Hydrochloride | 0.5 g |
| Asparagine Monohydrate | 0.5 g |
| Aspartic Acid | 0.5 g |
| Citrulline | 0.5 g |
| Cysteine | 0.5 g |
| β-3,4-Dihydroxyphenylalanine | 0.5 g |
| Glutamic Acid | 0.5 g |
| Glycine | 0.5 g |
| Histidine Hydrochloride | 0.5 g |
| Isoleucine | 0.5 g |
| Leucine | 0.5 g |
| Lysine Hydrochloride | 0.5 g |
| Methionine | 0.5 g |
| Norleucine | 0.5 g |
| Norvaline | 0.5 g |
| Ornithine Hydrochloride | 0.5 g |
| Phenylalanine | 0.5 g |
| Proline | 0.5 g |
| Serine | 0.5 g |

-continued

| Ingredient | Amount |
|---|---|
| Threonine | 0.5 g |
| Tryptophan | 0.5 g |
| Tyrosine | 0.5 g |
| Valine | 0.5 g |

The pH was adjusted to 7.1 with acetic acid and some undissolved material was filtered off.

To this dark brown test solution was added 0.2 g of polymer. The solution was stirred 3 hours, during which time the pH shifted to ~7.5 (and was not readjusted). The solid was filtered off and the iron content analyzed by atomic absorption spectroscopy at a commercial laboratory with the following results:

| Polymer | % Heme Remaining |
|---|---|
| Poly (Ammoniumhexylacrylamide) = Poly (AHA) | 55 |
| Poly (AEABPHA) | 66 |

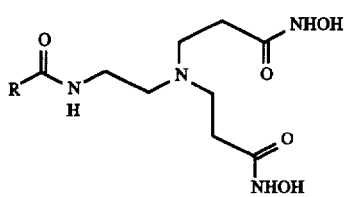

While it is evident that the polymers are not as effective as they are in the heme-iron only solution, they are still capable of binding a significant amount of heme.

Free Iron

One effective method of sequestering free iron involves attachment of classic iron chelators to a crosslinked polymer backbone. Iron chelators are typically small molecules that have between two and six subunits that attach themselves directly to the iron atom. Desferal® chelator (deferoxamine mesylate) is a good example. Good chelators contain such moieties as phenolates, enolic hydroxyls, ketones, aldehydes, carboxylates, phosphates and phosphonates, thiolates, sulfides and disulfides, hydroxamic acids and hydroxamates, amines, amides, and nitrones. The polymers can be designed such that the iron is chelated entirely by side chain groups:

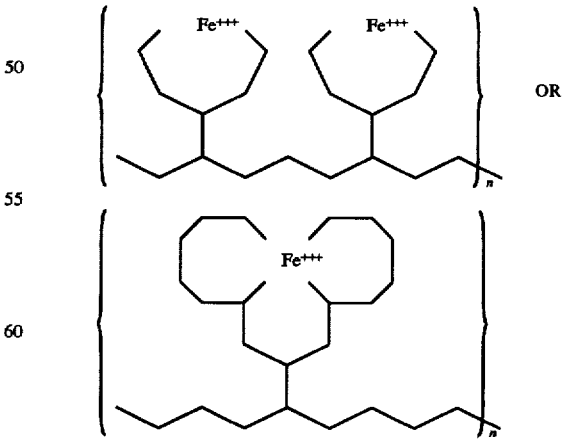

or such that it is chelated at least partially across the backbone:

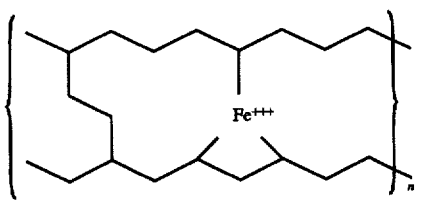

OR

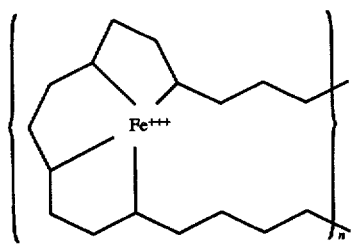

In order to assess the potential of each candidate polymer a test was devised to quantitate the binding of iron to the polymer. This test involved stirring the polymer in a solution designed to mimic physiologic conditions. The amount of iron chosen corresponds to ~9 mg of iron (a typical daily intake) and is dissolved in 1 L of fluid (the amount typically passing out of the small intestine in one day).

| Free Iron Test Solution | |
|---|---|
| NaCl | 20 g |
| $FeCl_3 \cdot 6H_2O$ | 0.13 g |
| Citric Acid | 0.09 g |
| Water | 3 L Total Volume |
| NaOH | Adjust to pH 7 |

Results are shown below for a variety of polymers.

| | % Free Iron Remaining | | | | |
|---|---|---|---|---|---|
| Polymer | 0.001 g | 0.002 g | 0.003 g | 0.005 g | 0.01 g |
| Poly(ethyleneimine) "A" | 16 | 15 | 1.5–6 | 0–5 | 0 |
| Poly(ethyleneimine) "B" | — | 63 | 66 | 48 | — |
| Poly(ethyleneimine) "C" | — | 3.5 | 2.6 | >2 | — |
| Colestid ® | 85 | — | — | 33 | 30 |

| | % Free Iron Remaining | | | | |
|---|---|---|---|---|---|
| Polymer | 0.01 g | 0.02 g | 0.03 g | 0.05 g | 0.1 g |
| Poly(diethylaminopropyl methacrylamide) | — | 32 | 1–23 | 0–11 | 1–39 |
| Poly(diethylenetriamine methacrylamide) | — | — | 12 | 3 | 3 |
| Colestid ® | 30 | <2 | <2 | <2 | <2 |
| Poly(PEH-acrylamide) | 29 | 5 | 2 | <2 | <2 |
| Poly(TAEA-acrylamide) | — | — | 31 | 35 | 26 |
| Poly(dimethylaminopropyl methacrylamide) | 22 | 2 | <2 | <2 | <2 |

| | Iron Binding | % Free Iron Remaining | | |
|---|---|---|---|---|
| Polymer | Group(s) | 0.03 g | 0.05 g | 0.1 g |
| Poly(mercaptoethyl-acrylamide) | R—SH | — | — | 44 |
| Poly(IAHH) | R—CONHOH; R—CO₂H | — | 57 | — |
| Poly(N-hydroxymethacrylamide) | R—CONHOH | 40 | 30 | 29 |
| Poly(N-methyl-N-hydroxy-methacrylamide) | $RCON(CH_3)OH$ | 6 | 6 | 8 |
| Poly(salicylic acrylamide) | 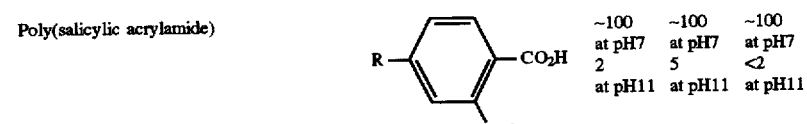 | ~100 at pH7 2 at pH11 | ~100 at pH7 5 at pH11 | ~100 at pH7 <2 at pH11 |
| Poly(3-hydroxyacrylamide) | 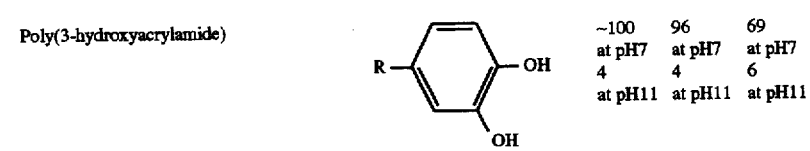 | ~100 at pH7 4 at pH11 | 96 at pH7 4 at pH11 | 69 at pH7 6 at pH11 |
| Poly(AEABMP) | several | — | 69 | — |

| Polymer | Structure | | | |
|---|---|---|---|---|
| Poly(AFABPHA) | R—NH—CH₂CH₂—N(CH₂CH₂C(O)OCH₃)₂ (several) | — | 25 | 7 |
| Poly(cholinevinylphosphonate) | R—NH—CH₂CH₂—N(CH₂CH₂C(O)NHOH)₂ | — | — | 82 using 0.2 g |
| Poly(N-imidazolepropyl-acrylamide) | R—P(=O)(O⁻)(OH) | — | — | 19 |
| | R—N(imidazole) | | | |
| Poly(ammoniumhexyl-acrylamide) | R—NH₂ | 21 | 6 | 14 |
| Poly(vinylamine) | R—NH₂ | — | <2 | — |
| Poly(diethylaminopropyl-methacrylamide) | R—N(CH₂CH₃)₂ | 4 | 11 | 9 |
| Poly(dimethylamino-propylacrylamide-hydrochloride) | R—N(CH₃)₂ | 23 | 17 | 12 |
| Poly(dimethylaminopropyl-methacrylamide-hydrochloride) | R—N(CH₃)₂ | 47 | 41 | 34 after water washes 8 |
| Poly(methacrylamidopropyl trimethylammonium chloride) | uncertain | 16 | 4 | 11 |

Clearly some of the polymers are more effective than others, with poly(vinylamine), poly(ethyleneimine), and poly(dimethylaminopropylmethacrylamide) being among the most effective.

Methods

Heme-Iron Assay

The polymer to be tested is ground and sieved to −80/+200 mesh size unless it is already a fine powder, in which case it is used as is. A measured amount of the polymer (typically 0.05–0.2 g) is suspended in 100 mL of the heme test solution. The pH is adjusted to 7.0 using either acetic acid or 1N NaOH as necessary. The mixture is then stirred for three hours, at the end of which the pH is again adjusted to 7.0. The solid is then filtered off using Whatman #1 filter paper, and the liquid is examined spectroscopically.

Heme-bound iron has a broad absorption at ~340–380 nm. The absorption is determined at 365 nm and corrected for a baseline absorption, typically by subtracting the average of the absorbances at 380 and 450 nm.

$$A_{365} = A_{365}(\text{measured}) - (A_{280} + A_{450})/2 \quad (1)$$

The concentration of heme iron is then determined by comparison to a standard curve made using the starting solution and various dilutions thereof by plotting the relationship between corrected absorbance and the concentration of heme iron. The relationship generally fits well by a straight line of the formula:

$$[Heme\ Fe] = 100\% \times [(0.189 \times A_{365}) + 0.001] \quad (2)$$

where the [Heme Fe] is the percent heme remaining by comparison to the starting heme solution.

Free Iron Assay

The free iron assay is similar to that used for heme iron. To 50 mL of the filtered iron test solution is added 3 mL of 0.3% aqueous o-phenanthroline and 1 mL of 10% aqueous hydroxylamine hydrochloride. The solution is stirred, and the pH is brought to 3.5 using aqueous sodium citrate (250 g/L) or 0.1N sulfuric acid, then diluted to a final volume of 60 mL. The solution is stirred for 5 minutes and then allowed to sit for 20 hours at room temperature. The absorbance is then read at 508 nm, with baseline points determined at 400 nm and 616 nm. The corrected absorbance at 508 nm is calculated by subtracting the average of the absorbances at 400 nm and 616 nm.

$$A_{508} = A_{508}(\text{measured}) - (A_{400} + A_{616})/2 \quad (3)$$

The relationship between $A_{508}$ and the free iron concentration is not a single straight line over the entire range of interest. The relationship is linear over three ranges and the linear least squares fits were used to derive the equations below:

| Range Applicable ($A_{508}$) | Equation | |
| --- | --- | --- |
| 0–0.008 | [Fe] = 333.3 ($A_{508}$) − 2.17 | (4) |
| 0.008–0.05 | [Fe] = 102.3 ($A_{508}$) − 0.30 | (5) |
| 0.05–1.1 | [Fe] = 92.3 ($A_{508}$) + 0.63 | (6) | where [Fe] is the % of free iron remaining compared to the original solution. Values of [Fe] below 2% are reported as "<2"% due to uncertainty in this range.

EXAMPLES OF POLYMER SYNTHESES

1. Preparation of Poly(vinylamine)

The first step involved the preparation of ethylidenebisacetamide. Acetamide (118 g), acetaldehyde (44.06 g), copper acetate (0.2 g), and water (300 mL) were placed in a 1 L three neck flask fitted with condenser, therometer, and mechanical stirrer. Concentrated HCl (34 mL) was added and the mixture was heated to 45°–50° C. with stirring for 24 hours. The water was then removed in vacuo to leave a thick sludge which formed crystals on cooling to 5° C. Acetone (200 mL) was added and stirred for a few minutes, after which the solid was filtered off and discarded. The acetone was cooled to 0° C. and solid was filtered off. This solid was rinsed in 500 mL acetone and air dried 18 hours to yield 31.5 g of ethylidenebisacetamide.

The next step involved the preparation of vinylacetamide from ethylidenebisacetamide.

Ethylidenebisacetamide (31.05 g), calcium carbonate (2 g) and celite 541 (2 g) were placed in a 500 mL three neck flask fitted with a thermometer, a mechanical stirrer, and a distilling head atop a Vigreux column. The mixture was vacuum distilled at 24 mm Hg by heating the pot to 180°–225° C. Only a single fraction was collected (10.8 g) which contained a large portion of acetamide in addition to the product (determined by NMR). This solid product was dissolved in isopropanol (30 mL) to form the crude solution used for polymerization.

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven to yield 0.8 g of poly(vinylacetamide), which was used to prepare poly(vinylamine) as follows.

Poly(vinylacetamide) (0.79 g) was placed in a 100 mL one neck flask containing water 25 mL and concentrated HCl 25 mL. The mixture was refluxed for 5 days, the solid was filtered off, rinsed once in water, twice in isopropanol, and dried in a vacuum oven to yield 0.77 g. The product of this reaction (~0.84 g) was suspended in NaOH (46 g) and water (46 g) and heated to boiling (~140° C.). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then the isopropanol, and dried in a vacuum oven to yield 0.51 g.

2. Preparation of Poly(ethyleneimine)

Polyethyleneimine (120 g of a 50% aqueous solution; Scientific Polymer Products) was dissolved in water (250 mL). Epichlorohydrin (22.1 mL) was added dropwise. The solution was heated to 60° C. for 4 hours, after which it had gelled. The gel was removed, blended with water (1.5 L) and the solid was filtered off, rinsed three times with water (3 L) and twice with isopropanol (3 L), and the resulting gel was dried in a vacuum oven to yield 81.2 g of the title polymer.

3. Preparation of Poly(allylamine)Hydrochloride

To a 2 liter, water-jacketed reaction kettle equipped with (1) a condenser topped with a nitrogen gas inlet, (2) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 g) was added dropwise with stirring while maintaining the reaction temperature at 5°–10° C. After addition was complete, the mixture was removed, placed in a 3 liter one-neck flask, and 206 g of liquid was removed by rotary vacuum evaporation at 60° C. Water (20 mL) was then added and the liquid was returned to the reaction kettle. Azobis (amidinopropane)dihydrochloride (0.5 g) suspended in 11 mL of water was then added. The resulting reaction mixture was heated to 50° C. under a nitrogen atmosphere with stirring for 24 hours. Additional azobis(amidinopropane) dihydrochloride (5 mL) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, re-suspended in methanol (4 L), stirred for 1 hour, and collected by filtration. The methanol rinse was then repeated one more time and the solid dried in a vacuum oven to afford 215.1 g of poly(allylamine)hydrochloride as a granular white solid.

4. Preparation of Poly(allylamine)Hydrochloride Crosslinked with Epichlorohydrin To a 5 gallon vessel was added poly(allylamine) hydrochloride prepared as described in Example 3 (1 kg) and water (4 L). The mixture was stirred to dissolve the hydrochloride and the pH was adjusted by adding solid NaOH (284 g). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield about 677 g of the cross linked polymer as a granular, brittle, white solid.

5. Preparation of Poly(allylamine)Hydrochloride Crosslinked with Butanedioldiglycidyl Ether To a 5 gallon plastic bucket was added poly(allylamine) hydrochloride prepared as described in Example 3 (500 g) and water (2 L). The mixture was stirred to dissolve the hydrochloride and the pH was adjusted to 10 by adding solid NaOH (134.6 g). The resulting solution was cooled to room temperature in the bucket, after which 1,4-butanedioldiglycidyl ether crosslinking agent (65 mL) was added all at once with stirring. The resulting mixture was stirred gently until it gelled (about 6 minutes). The crosslinking reaction was allowed to proceed for an additional 18 hours at room temperature, after which the polymer gel was removed and dried in a vacuum oven at 75° C. for 24 hours. The dry solid was then ground and sieved to −30 mesh, after which it was suspended in 6 gallons of water and stirred for 1 hour. The solid was then filtered off and the rinse process repeated two more times. The resulting solid was then air dried for 48 hours, followed by drying in a vacuum oven at 50° C. for 24 hours to yield about 415 g of the crosslinked polymer as a white solid.

6. Preparation of Poly(allylamine)Hydrochloride Crosslinked with Ethanedioldiglycidyl Ether To a 100 mL beaker was added poly(allylamine) hydrochloride prepared as described in Example 3 (10 g) and water (40 mL). The mixture was stirred to dissolve the hydrochloride and the pH was adjusted to 10 by adding solid NaOH. The resulting solution was cooled to room temperature in the beaker, after which 1,2-ethanedioldiglycidyl ether crosslinking agent (2.0 mL) was added all at once with stirring. The resulting mixture was stirred gently until it gelled (about 4 minutes). The crosslinking reaction was allowed to proceed for an additional 18 hours at room temperature, after which the polymer gel was removed and blended in 500 mL of methanol. The solid was then filtered off and suspended in water (500 mL). After stirring for 1 hour, the solid was filtered off and the rinse process repeated. The resulting solid was rinsed twice in isopropanol (400 mL) and then dried in a vacuum oven at 50° C. for 24 hours to yield 8.7 g of the crosslinked polymer as a white solid.

7. Preparation of Poly(allylamine)Hydrochloride Crosslinked with Dimethylsuccinate To a 500 mL round bottom flask was added poly (allylamine)hydrochloride prepared as described in Example 3 (10 g), methanol (100 mL), and triethylamine (10 mL). The mixture was stirred and dimethylsuccinate crosslinking agent (1 mL) was added. The solution was heated to reflux and the stirring discontinued after 30 minutes. After 18 hours, the solution was cooled to room temperature, and the solid filtered off and blended in 400 mL of isopropanol. The solid was then filtered off and suspended in water (1 L). After stirring for 1 hour, the solid was filtered off and the rinse process repeated two more times. The solid was then rinsed once in isopropanol (800 mL) and dried in a vacuum oven at 50° C. for 24 hours to yield 5.9 g of the crosslinked polymer as a white solid.

8. Preparation of Poly(ethyleneimine) Crosslinked with Acryloyl Chloride

Into a 5 L three neck flask equipped with a mechanical stirred, a thermometer, and an addition funnel was added poly(ethyleneimine) (510 g of a 50% aqueous solution, equivalent to 255 g of dry polymer) and isopropanol (2.5 L). Acryloyl chloride crosslinking agent (50 g) was added dropwise through the addition funnel over a 35 minute period while maintaining the temperature below 29° C. The solution was then heated to 60° C. with stirring for 18 hours, after which the solution was cooled and the solid immediately filtered off. The solid was then washed three times by suspending it in water (2 gallons), stirring for 1 hour, and filtering to recover the solid. Next, the solid was rinsed once by suspending it in methanol (2 gallons), stirring for 30 minutes, and filtering to recover the solid. Finally, the solid was rinsed in isopropanol as in Example 7 and dried in a vacuum oven at 50° C. for 18 hours to yield 206 g of the crosslinked polymer as a light orange granular solid.

9. Alkylation of Poly(allylamine) Crosslinked with Butanedioldiglydicyl ether with 1-iodooctane Alkylating Agent Poly(allylamine) crosslinked with butanedioldiglycidyl ether prepared as described in Example 5 (5 g) was suspended in methanol (100 mL) and sodium hydroxide (0.2 g) was added. After stirring for 15 minutes, 1-iodooctane (1.92 mL) was added and the mixture stirred at 60° C. for 20 hours. The mixture was then cooled and the solid filtered off. Next, the solid was washed by suspending it in isopropanol (500 mL), after which it was stirred for 1 hour and then collected by filtration. The wash procedure was then repeated twice using aqueous sodium chloride (500 mL of a 1M solution), twice with water (500 mL), and once with isopropanol (500 mL) before drying in a vacuum oven at 50° C. for 24 hours to yield 4.65 g of alkylated product.

The procedure was repeated using 2.88 mL of 1-iodooctane to yield 4.68 g of alkylated product.

10. Alkylation of Poly(allylamine) Crosslinked with Epichlorohydrin with 1-iodooctane Alkylating Agent Poly(allylamine) crosslinked with epichlorohydrin prepared as described in Example 4 (5 g) was alkylated according to the procedure described in Example 9 except that 3.84 mL of 1-iodooctane was used. The procedure yielded 5.94 g of alkylated product.

11. Alkylation of Poly(allylamine) Crosslinked with Epichlorohydrin with 1-iodooctadecane Alkylating Agent Poly(allylamine) crosslinked with epichlorohydrin prepared as described in Example 4 (10 g) was suspended in methanol (100 mL) and sodium hydroxide (0.2 g) was added. After stirring for 15 minutes, 1-iodooctadecane (8.1 g) was added and the mixture stirred at 60° C. for 20 hours. The mixture was then cooled and the solid filtered off. Next, the solid was washed by suspending it in isopropanol (500 mL), after which it was stirred for 1 hour and then collected by filtration. The wash procedure was then repeated twice using aqueous sodium chloride (500 mL of a 1M solution), twice with water (500 mL), and once with isopropanol (500 mL) before drying in a vacuum oven at 50° C. for 24 hours to yield 9.6 g of alkylated product.

12. Alkylation of Poly(allylamine) Crosslinked with Butanedioldiglycidyl Ether with 1-iodododecane Alkylating Agent Poly(allylamine) crosslinked with butanedioldiglycidyl ether prepared as described in Example 5 (5 g) was alkylated according to the procedure described in Example 11 except that 2.47 mL of 1-iodododecane was used. The procedure yielded 4.7 g of alkylated product.

13. Alkylation of Poly(allylamine) Crosslinked with Butanedioldiglycidyl Ether with Benzyl Bromide Alkylating Agent Poly(allylamine) crosslinked with butanedioldiglycidyl ether prepared as described in Example 5 (5 g) was alkylated according to the procedure described in Example 11 except that 2.42 mL of benzyl bromide was used. The procedure yielded 6.4 g of alkylated product.

14. Alkylation of Poly(allylamine) Crosslinked with Epichlorohydrin with Benzyl Bromide Alkylating Agent Poly(allylamine) crosslinked with epichlorohydrin prepared as described Example 4 (5 g) was alkylated according to the procedure described in Example 11 except that 1.21 mL of benzyl bromide was used. The procedure yielded 6.6 g of alkylated product.

15. Alkylation of Poly(allylamine) Crosslinked with Epichlorohydrin with 1-iododecane Alkylating Agent Poly(allylamine) crosslinked with epichlorohydrin prepared as described in Example 4 (20 g) was alkylated according to the procedure described in Example 11 except that 7.15 g of 1-iododecane and 2.1 g of NaOH were used. The procedure yielded 20.67 g of alkylated product.

16. Alkylation of Poly(allylamine) Crosslinked with Epichlorohydrin with 1-iodobutane Alkylating Agent Poly(allylamine) crosslinked with epichlorohydrin prepared as described in Example 4 (20 g) was alkylated according to the procedure described in Example 11 except that 22.03 g of 1-iodobutane and 8.0 g of NaOH were used. The procedure yielded 24.0 g of alkylated product.

The procedure was also followed using 29.44 g and 14.72 g of 1-iodobutane to yield 17.0 g and 21.0 g, respectively, of alkylated product.

17. Alkylation of Poly(allylamine) Crosslinked with Epichlorohydrin with 1-iodotetradecane Alkylating Agent Poly(allylamine) crosslinked with epichlorohydrin prepared as described in Example 4 (5 g) was alkylated according to the procedure described in Example 11 except that 2.1 mL of 1-iodotetradecane was used. The procedure yielded 5.2 g of alkylated product.

The procedure was also followed using 6.4 mL of 1-iodotetradecane to yield 7.15 g of alkylated product.

18. Alkylation of Poly(allylamine) Crosslinked with Epichlorohydrin with 1-iodooctane Alkylating Agent Poly(allylamine) crosslinked with epichlorohydrin prepared as described in Example 4 (5 g) was alkylated according to the procedure described in Example 11 except that 1.92 mL of 1-iodooctane was used. The procedure yielded 5.0 g of alkylated product.

19. Alkylation of a Copolymer of Diethylene Triamine and Epichlorohydrin with 1-iodooctane Alkylating Agent A copolymer of diethylene triamine and epichlorohydrin (10 g) was alkylated according to the procedure described in Example 11 except that 1.92 mL of 1-iodooctane was used. The procedure yielded 5.3 g of alkylated product.

20. Alkylation of Poly(allylamine) Crosslinked with Epichlorohydrin with 1-iodododecane and Glycidylpropyltrimethylammonium Chloride Alkylating Agents Poly(allylamine) crosslinked with epichlorohydrin prepared as described in Example 4 (20 g) was alkylated according to the procedure described in Example 11 except that 23.66 g of 1-iodododecane, 6.4 g of sodium hydroxide, and 500 mL of methanol were used. 24 grams of the alkylated product was then reacted with 50 g of 90% glycidylpropyltrimethylammonium chloride in methanol (1 L). The mixture was stirred at reflux for 24 hours, after which it was cooled to room temperature and washed successively with water (three times using 2.5 L each time). Vacuum drying afforded 22.4 g of dialkylated product.

Dialkylated products were prepared in an analogous manner by replacing 1-iodododecane with 1-iodooctane and 1-iodooctadecane, respectively, followed by alkylation with glycidylpropyltrimethylammonium chloride.

21. Alkylation of Poly(allylamine) Crosslinked with Epichlorohydrin with Glycidylpropyltrimethylammonium Chloride Alkylating Agent Poly(allylamine) crosslinked with epichlorohydrin prepared as described in Example 4 (5 g) was reacted with 11.63 g of 90% glycidylpropyltrimethylammonium chloride (1 mole equiv.) in methanol (100 mL). The mixture was stirred at 60° C. for 20 hours, after which it was cooled to room temperature and washed successively with water (three times using 400 mL each time) and isopropanol (one time using 400 mL). Vacuum drying afforded 6.93 g of alkylated product.

Alkylated products were prepared in an analogous manner using 50%, 200%, and 300% mole equiv of 90% glycidylpropyltrimethylammonium chloride.

22. Alkylation of Poly(allylamine) Crosslinked with Epichlorohydrin with (10-bromodecyl)trimethylammonium Bromide Alkylating Agent The first step is the preparation of (10-bromodecyl)trimethylammonium bromide as follows.

1,10-dibromodecane (200 g) was dissolved in methanol (3 L) in a 5 liter three neck round bottom flask fitted with a cold condenser (−5° C.). To this mixture was added aqueous trimethylamine (176 mL of a 24% aqueous solution, w/w). The mixture was stirred at room temperature for 4 hours, after which is was heated to reflux for an additional 18 hours. At the conclusion of the heating period, the flask was cooled to 50° C. and the solvent removed under vacuum to leave a solid mass. Acetone (300 mL) was added and the mixture stirred at 40° C. for 1 hour. The solid was filtered off, resuspended in an additional portion of acetone (1 L), and stirred for 90 minutes.

At the conclusion of the stirring period, the solid was filtered and discarded, and the acetone fractions were combined and evaporated to dryness under vacuum. Hexanes (about 1.5 L) were added and the mixture then stirred for 1 hour, after which the solid was filtered off and then rinsed on the filtration funnel with fresh hexanes. The resulting solid was then dissolved in isopropanol (75 mL) at 40° C. Ethyl acetate (1500 mL) was added and the temperature raised to about 50° C. to fully dissolve all solid material. The flask was then wrapped in towels and placed in a freezer for 24 hours, resulting in the formation of solid crystals. The crystals were filtered off, rinsed in cold ethyl acetate, and dried in a vacuum oven at 75° C. to yield 100.9 g of (10-bromodecyl)trimethylammonium bromide as white crystals.

Poly(allylamine) crosslinked with epichlorohydrin prepared as described in Example 4 (10 g) was suspended in methanol (300 mL). Sodium hydroxide (3.3 g) was added and the mixture stirred until it dissolved. (10-bromodecyl)trimethylammonium bromide (20.7 g) was added and the mixture was refluxed with stirring for 20 hours. The mixture was then cooled to room temperature and washed successively with methanol (two times using 1 L each time), sodium chloride) (two times using 1 L of 1M solution each time), water (three times using 1 L each time), and isopropanol (one time using 1 L). Vacuum drying yielded 14.3 g of alkylated product.

23. Alkylation of Poly(allylamine) Crosslinked with Epichlorohydrin with (10-bromodecyl)trimethylammonium Bromide and 1,10-dibromodecane Alkylating Agents 1,10-dibromodecane (200 g) was dissolved in methanol (3 L) in a 5 liter round bottom flask fitted with a cold condenser (−5° C.). To this mixture was added aqueous trimethylamine (220 mL of a 24% aqueous solution, w/w). The mixture was stirred at room temperature for 4 hours, after which it was heated to reflux for an additional 24 hours. The flask was then cooled to room temperature and found to contain 3350 mL of clear liquid.

Poly(allylamine) crosslinked with epichlorohydrin prepared as described in Example 4 (30 g) was suspended in the clear liquid (2 L) and stirred for 10 minutes. Sodium hydroxide (20 g) was then added and the mixture stirred until it had dissolved. Next, the mixture was refluxed with stirring for 24 hours, cooled to room temperature, and the solid filtered off. The solid was then washed successively with methanol (one time using 10 L), sodium chloride (two times using 10 L of a 1M solution each time), water (three times using 10 L each time), and isopropanol (one time using 5 L). Vacuum drying afforded 35.3 g of dialkylated product.

24. Alkylation of Poly(allylamine) Crosslinked with Epichlorohydrin with (10-bromodecyl)trimethylammonium Bromide and 1-bromodecane Alkylating Agents Poly(allylamine) crosslinked with epichlorohydrin prepared as described in Example 4 (10 g) was suspended in methanol (300 mL). Sodium hydroxide (4.99 g) was added and the mixture stirred until it dissolved. (10-bromodecyl) trimethylammonium bromide prepared as described in Example 22 (20.7 g) and 1-bromodecane were added and the mixture was refluxed with stirring for 20 hours. The mixture was then cooled to room temperature and washed successively with methanol (two times using 1 L each time), sodium chloride (two times using 1 L of a 1M solution each time), water (three times using 1 L each time), and isopropanol (one time using 1 L). Vacuum drying yielded 10.8 g of dialkylated product.

Dialkylated products were also prepared in analogous fashion using different amounts of 1-bromodecane as follows: (a) 3.19 g 1-bromodecane and 4.14 g sodium hydroxide to yield 11.8 g of dialkylated product; (b) 38.4 g 1-bromodecane and 6.96 g sodium hydroxide to yield 19.1 g of dialkylated product.

Dialkylated products were also prepared in analogous fashion using the following combinations of alkylating agents:

1-bromodecane and (4-bromobutyl)trimethylammonium bromide; 1-bromodecane and (6-bromohexyl)trimethylammonium bromide; 1-bromodecane and (8-bromooctyl)trimethylammonium bromide; 1-bromodecane and (2-bromoethyl)trimethylammonium bromide; 1-bromodecane and (3-bromopropyl)trimethylammonium bromide; 1-bromohexane and (6-bromohexyl)trimethylammonium bromide; 1-bromododecane and (12-bromododecyl)trimethylammonium bromide; and 1-bromooctane and (6-bromohexyl)trimethylammonium bromide.

25. Alkylation of Poly(allylamine) Crosslinked with Epichlorohydrin with 11-bromo-1-undecanol Alkylating Agent Poly(allylamine) crosslinked with epichlorohydrin prepared as described in Example 4 (5.35 g) was suspended in methanol (100 mL). Sodium hydroxide (1.10 g) was added and the mixture stirred until it dissolved. 11-bromo-1-undecanol (5.0 g) was added and the mixture was refluxed with stirring for 20 hours, after which it was cooled to room temperature and washed successively with methanol (one time using 3 L), sodium chloride (two times using 500 mL of a 1M solution each time), and water (three times using 1 L each time). Vacuum drying yielded 6.47 g of alkylated product.

The reaction was also performed using 1.05 g sodium hydroxide and 10 g 11-bromo-1-undecanol to yield 8.86 g of alkylated product.

26. Alkylation of Poly(allylamine) Crosslinked with Epichlorohydrin with N-(2,3-epoxypropane)butyramide Alkylating Agent The first step is the preparation of N-allyl butyramide as follows.

Butyroyl chloride (194.7 g, 1.83 mol) in 1 L of tetrahydrofuran was added to a three neck round bottom flask equipped with a thermometer, stir bar, and dropping funnel. The contents of the flask were then cooled to 15° C. in an ice bath while stirring. Allylamine (208.7 g, 3.65 mol) in 50 mL of tetrahydrofuran was then added slowly through the dropping funnel while maintaining stirring. Throughout the addition, the temperature was maintained at 15° C. After addition was complete, stirring continued for an additional 15 minutes, after which the solid allylamine chloride precipitate was filtered off. The filtrate was concentrated under vacuum to yield 236.4 g of N-allyl butyramide as a colorless viscous liquid.

N-allyl butyramide (12.7 g, 0.1 mol) was taken into a 1 L round bottom flask equipped with a stir bar and air condenser. Methylene chloride (200 mL) was added to the flask, followed by 3-chloroperoxybenzoic acid (50–60% strength, 200 g) in five portions over the course of 30 minutes and the reaction allowed to proceed. After 16 hours, TLC analysis (using 5% methanol in dichloromethane) showed complete formation of product. The reaction mixture was then cooled and filtered to remove solid benzoic acid precipitate. The filtrate was washed with saturated sodium sulfite solution (two times using 100 mL each time) and then with saturated sodium bicarbonate solution (two times using 100 mL each time). The dichloromethane layer was then dried with anhydrous sodium sulfate and concentrated under vacuum to yield 10.0 g of N-(2,3-epoxypropane)butyramide as a light yellow viscous liquid.

Poly(allylamine) crosslinked with epichlorohydrin prepared as described in Example 4 (10 g, −80 sieved) and methanol (250 mL) were added to a 1 L round bottom flask, followed by N-(2,3-epoxypropane)butyramide (0.97 g, 0.0067 mol, 5 mol %) and then sodium hydroxide pellets (0.55 g, 0.01375 mol). The mixture was stirred overnight at room temperature. After 16 hours, the reaction mixture was filtered and the solid washed successively with methanol (three times using 300 mL each time), water (two times using 300 mL each time), and isopropanol (three times using 300 mL each time. Vacuum drying at 54° C. overnight yielded 9.0 g of the alkylated product as a light yellow powder.

Alkylated products based upon 10 mol %, 20 mol %, and 30 mol % N-(2,3-epoxypropane)butyramide were prepared in analogous fashion except that (a) in the 10 mol % case, 1.93 g (0.013 mol) N-(2,3-epoxypropane)butyramide and 1.1 g (0.0275 mol) sodium hydroxide pellets were used to yield 8.3 g of alkylated product, (b) in the 20 mol % case, 3.86 g (0.026 mol) N-(2,3-epoxypropane)butyramide and 2.1 g (0.053 mol) sodium hydroxide pellets were used to yield 8.2 g of alkylated product, and (c) in the 30 mol % case, 5.72 g (0.04 mol) N-(2,3-epoxypropane)butyramide and 2.1 g (0.053 mol) sodium hydroxide pellets were used to yield 8.32 g of alkylated product.

27. Alkylation of Poly(allylamine) Crosslinked with Epichlorohydrin with N-(2,3-epoxypropane)Hexanamide Alkylating Agent The first step is the preparation of N-allyl hexanamide as follows. p Hexanoyl chloride (33 g, 0.25 mol) in 250 mL of tetrahydrofuran was added to a three neck round bottom flask equipped with a thermometer, stir bar, and dropping funnel. The contents of the flask were then cooled to 15° C. in an ice bath while stirring. Allylamine (28.6 g, 0.5 mol) in 200 mL of tetrahydrofuran was then added slowly through the dropping funnel while maintaining stirring. Throughout the addition, the temperature was maintained at 15° C. After addition was complete, stirring continued for an additional 15 minutes, after which the solid allylamine chloride precipitate was filtered off. The filtration was concentrated under vacuum to yield 37 g of N-allyl hexanamide as a colorless viscous liquid.

N-allyl hexanamide (16 g, 0.1 mol) was taken into a 1 L round bottom flask equipped with a stir bar and air condenser. Methylene chloride (200 mL) was added to the flask, followed by 3-chloroperoxybenzoic acid (50–60% strength, 200 g) in five portions over the course of 30 minutes and the reaction allowed to proceed. After 16 hours, TLC analysis (using 5% methanol in dichloromethane) showed complete formation of product. The reaction mixture was then cooled and filtered to remove solid benzoic acid precipitate. The filtrate was washed with saturated sodium sulfite solution (two times using 100 mL each time) and then with saturated sodium bicarbonate solution (two times using 100 mL each time). The dichloromethane layer was then dried with anhydrous sodium sulfate and concentrated under vacuum to yield 14.2 g of N-(2,3-epoxypropane)hexanamide as a light yellow viscous liquid.

Poly(allylamine) crosslinked with epichlorohydrin prepared as described in Example 4 (10 g, −80 sieved) and methanol (250 mL) were added to a 1 L round bottom flask, followed by N-(2,3-epoxypropane)hexanamide (4.46 g, 0.026 mol, 20 mol %) and then sodium hydroxide pellets (2.1 g, 0.053 mol). The mixture was stirred overnight at room temperature. After 16 hours, the reaction mixture was filtered and the solid washed successively with methanol (three times using 300 mL each time), water (two times using 300 mL each time), and isopropanol (three times using 300 mL each time. Vacuum drying at 54° C. overnight yielded 9.59 g of the alkylated product as a light yellow powder.

An alkylated product based upon 30 mol % N-(2,3-epoxypropane)hexanamide was prepared in analogous fashion except that 6.84 g (0.04 mol) N-(2,3-epoxypropane) hexanamide was used to yield 9.83 g of alkylated product.

28. Alkylation of Poly(allylamine) Crosslinked with Epichlorohydrin with (6-Bromohexyl)trimethylammonium Bromide and 1-bromodecane Alkylating Agent To a 12-L round bottom flask equipped with a mechanical stirrer, a thermometer, and a condenser is added methanol (5 L) and sodium hydroxide (133.7 g). The mixture is stirred until the solid has dissolved and crosslinked poly (allylamine) (297 g; ground to −80 mesh size) is added along with additional methanol (3 L). (6-Bromohexyl) trimethylammonium bromide (522.1 g) and 1-bromodecane (311.7 g) are added and the mixture heated to 65° C. with stirring. After 18 hours at 65° C. the mixture is allowed to cool to room temperature. The solid is filtered off and rinsed by suspending, stirring for 30 minutes, and filtering off the solid from: methanol, 12 L; methanol, 12 L; 2M aqueous NaCl, 22 L; 2M aqueous NaCl, 22 L; deionized water, 22 L; deionized water, 22 L; deionized water, 22 L and isopropanol, 22 L. The solid is dried in a vacuum oven at 50° C. to yield 505.1 g of off-white solid. The solid is then ground to pass through an 80 mesh sieve.

29. Poly(ethyleneimine)"A"

Polyethyleneimine (50 9 of a 50% aqueous solution; Scientific Polymer Products) was dissolved in water (100 mL). Epichlorohydrin (4.6 mL) was added dropwise. The solution was heated to 55° C. for 4 hours, after which it had gelled. The gel was removed, blended with water (1 L) and the solid was filtered off, the rinse repeated once with water and twice with isopropanol, and the resulting gel was dried in a vacuum oven to yield 26.3 g of a rubbery solid.

30. Poly(ethyleneimine)"B" and Poly(ethyleneimine)"C"

Poly(ethyleneimine)"B" and Poly(ethyleneimine)"C" were made in a similar manner, except using 9.2 and 2.3 mL of epichlorohydrin, respectively.

31. Poly(methylmethacrylate-co-divinylbenzene)

Methylmethacrylate (50 g) and divinylbenzene (5 g) and azobisisobutyronitrile (AIBN; 1.0 g) were dissolved in isopropanol (500 mL) and heated to reflux for 18 hours under a nitrogen atmosphere. The solid white precipitate was filtered off, rinsed once in acetone (collected by centrifugation), once in water (collected by filtration and dried in a vacuum oven to yield 19.4 g.

32. Poly(diethylenetriaminemethacrylamide)

Poly(methylmethacrylate-co-divinylbenzene) (20 g) was suspended in diethylenetriamine (200 mL) and heated to reflux under a nitrogen atmosphere for 18 hours. The solid was collected by filtration, resuspended in water (500 mL), filtered off, resuspended in water (500 mL), collected by filtration, rinsed briefly in isopropanol, and dried in a vacuum oven to yield 18.0 g.

33. Poly(diethylaminopropylmethacrylamide)

Poly(methylmethacrylate-co-divinylbenzene) (20 g) was suspended in diethylaminopropylamine (200 mL) and heated to reflux under a nitrogen atmosphere for 18 hours. The solid was collected by filtration, resuspended in water (500 mL), filtered off, resuspended in water (500 mL), collected by filtration, rinsed briefly in isopropanol, and dried in a vacuum oven to yield 8.2 g.

34. Poly(dimethylaminopropylacrylamide)

Dimethylaminopropylacrylamide (10 g) and methylenebisacrylamide (1.1 g) were dissolved in water (50 mL) in a 100 mL three neck flask. The solution was stirred under nitrogen for 10 minutes. Potassium persulfate (0.3 g) and sodium metabisulfite (0.3 g) were each dissolved in water (2–3 mL) and then mixed. After a few seconds this solution was added to the monomer solution, still under nitrogen. A gel formed immediately and was allowed to sit overnight. The gel was removed and blended with isopropanol (500 mL). The solid was filtered off and rinsed three times with acetone. The solid white powder was filtered off and dried in a vacuum oven to yield 6.1 g.

35. Poly(N-hydroxymethacrylamide)

Poly(methylmethacrylate) (5.5 g; ground and sieved to −80/+200 mesh size) was put into a 500 mL three neck flask fitted with a thermometer and reflux condenser. Hydroxylamine hydrochloride (14 g) was dissolved in boiling methanol (72 mL) and added to the polymer while still hot. Potassium hydroxide (17 g) was dissolved in boiling methanol (43 mL) and also added to the polymer solution while hot. Methanol (50 mL) was added and the mixture was refluxed under a nitrogen atmosphere for 24 hours. After cooling, water was added to a total volume of 500 mL. The solid was collected by centrifugation and resuspended in water (800 mL). The pH of the solution was adjusted to 7.0 with acetic acid and the solid collected by centrifugation. After resuspension and centrifugation from water (800 mL), the solid was rinsed three times with isopropanol (1 L, 300 mL, 300 mL, respectively) the solid was collected by filtration and dried in a vacuum oven to yield 2.6 g.

36. Ammoniumethylacrylamide (AEA)

Acryloyl chloride (45.75 g) was dissolved in tetrahydrofuran (THF; 400 mL) in a 1 L flask. The solution was cooled to 8° C. in an ice bath and ethylenediamine (28.85 g) in THF (400 mL) was added dropwise, keeping the temperature at 8°–10° C. After addition the solution was stirred for 5 minutes and the solid was collected by filtration, washed three times in THF (50 mL), and dried in a vacuum oven to yield 74 g.

37. Ammoniumbutylacrylamide (ABA)

Acryloyl chloride (45.26 g) was dissolved in THF (400 mL) in a 1 L flask. The solution was cooled to 10° C. in an ice bath and butanediamine (42.3 g) in THF (100 mL) was added dropwise. After addition the solid was collected by filtration, washed three times in THF (50 mL), and dried in a vacuum oven to yield 80.9 g.

38. Ammoniumhexylacrylamide (AHA)

Hexanediamine (30 g) dissolved in THF (100 mL) was added dropwise to acryloyl chloride (23.4 g) dissolved in THF (300 mL) in an ice bath, keeping the temperature below 15° C. The solid that formed was filtered off, rinsed twice with THF, and dried in a vacuum oven to yield 48.5 g.

39. Dodecylacrylamide

Acryloyl chloride (19 g) was dissolved in THF (200 mL) in a 1 L flask and placed in an ice bath. A solution containing dodecylamine (37.1 g), triethylamine (20.2 g) and THF (300 mL) was added dropwise, maintaining the temperature at 5°–15° C. After addition the solution was stirred for 5 minutes and the solid was filtered off and discarded. The solvent was removed in vacuo from the mother liquor and methanol (50 mL) was added to the residue. After stirring, water (200 mL) was added and crystals formed. Additional water (200 mL) was added, the solution was stirred for 30 minutes, and the solid was filtered off. The solid was vacuum dried at room temperature to yield 40.3 g.

40. Poly(AEA)

AEA (20 g) and methylenebisacrylamide (2.2 g) were dissolved in warm water (32° C.; 100 mL). Potassium persulfate (0.2 g) was added with stirring. After 5 minutes potassium metabisulfite (0.2) was added with continued stirring. Within 5 minutes curds of polymer had formed. The solution was allowed to sit for 4 hours and was then broken up and stirred in water (700 mL) for 1 hour followed by filtration. The solid was then resuspended and filtered twice more with water (500 mL) and three times with isopropanol (500 mL). The solid was then vacuum dried to yield 11.0 g.

41. Copoly(AEA/allyl acrylamide)

Several copolymers were formed by substituting allylacrylamide for some portion of the AEA in the above procedure. Portions used were 20 g AEA/0 g allylacrylamide, 15 g AEA/5 g allylacrylamide, 10 g AEA/10 g allylacrylamide, and 5 g AEA/15 g allylacrylamide. Yields were 11.0, 10.8, 10.8 and 10.6 g respectively.

42. Poly(AEA/polyethyleneglycol dimethacrylate)

AEA (10 g), polyethylene glycol dimethacrylate (10 g; mw=600), and 0.32 g AIBN were suspended in dimethylsulfoxide (50 mL). The mixture was slowly heated under a nitrogen atmosphere. Gel formation started before all AEA was dissolved. The gel was kept at 90° C. for 60 minutes and then cooled under nitrogen. After sitting overnight the gel was removed, blended with isopropanol (500 mL), and the solid was collected by filtration. The solid was rinsed three times with water (500 mL), three times with isopropanol (500 mL) and dried in a vacuum oven to yield 13.45 g.

43. Poly(ABA)

ABA (27.0 g), methylenebisacrylamide (3.0 g), water (250 mL), and methanol (100 mL) were mixed together and warmed (35° C.) to dissolve. A small amount of insolubles were filtered off. Potassium persulfate (0.3 g) and potassium metabisulfite (0.3 g) were each dissolved in water (a few mL) and added to the monomer solution. After 4 hours the mixture was blended with isopropanol (500 mL) twice and dried in a vacuum oven to yield 21.4 g. The solid (21.4 g) was suspended three times in water (2 L), and collected by filtration each time. The solid was then rinsed in isopropanol (1 L) and dried in a vacuum oven to yield 17.2 g.

Alternatively, to yield a 5% crosslinked polymer instead of the 10% crosslinked polymer made above the same procedure was carried out using 28.5 g of monomer and 1.5 g of crosslinker. The final yield was 15.9 g.

44. Poly(AHA)

AHA (40 g) and methylenebisacrylamide (4.4 g) were dissolved in a warm mixture containing water (200 mL) and methanol (200 mL). Potassium persulfate (0.4 g) and potassium metabisulfite (0.4 g) were each dissolved in water (3 mL). After dissolving they were mixed together and within a few seconds added to the warm monomer solution. Curds of polymer formed immediately and within 2 minutes the solution had gelled. The solution was allowed to sit overnight and was then stirred in water (1.5 L) for 1 hour followed by filtration. The solid was rinsed twice with water, three times with methanol, and three times with isopropanol before being dried in a vacuum oven to yield 24.0 g.

45. Poly(dimethylaminopropylacrylamide hydrochloride)

Dimethylaminopropyl-acrylamide (20.10 g) was dissolved in water (100 mL) and neutralized with concentrated HCl to pH 6.95. Methylenebisacrylamide (2.2 g) and water (100 mL) were added and warmed (34° C.) to dissolve. Potassium persulfate (0.2 g) and potassium metabisulfite (0.2 g) were added with stirring. After gelation, the solution was allowed to sit for 6 hours, was blended with isopropanol (600 mL) three times, and dried in a vacuum oven to yield 14.47 g.

46. Poly(dimethylaminopropylmethacrylamide hydrochloride)

Dimethylaminopropylmethacrylamide (20.0 g) was dissolved in water (100 mL) and neutralized with concentrated HCl to pH 6.94. Methylenebisacrylamide (2.2 g) was added and the solution was warmed (39° C.) to dissolve. Potassium persulfate (0.3 g) and potassium metabisulfite (0.3 g) were added with stirring under a nitrogen atmosphere. After gelation, the solution was allowed to sit overnight, was blended with isopropanol (500 mL) twice, and dried in a vacuum oven to yield 27.65 g. Some of the solid (3.2 g; sieved to –80/+200 mesh size) was stirred in water (100 mL) for 50 minutes, additional water (100 mL) was added and the solution stirred for 36 minutes. The solid was collected by centrifugation, resuspended in water (400 mL), stirred 150 minutes, and again collected by centrifugation. The solid was finally resuspended in water (500 mL), stirred 90 minutes and collected by filtration. The solid was dried in a vacuum oven to yield 0.28 g.

47. Copoly(AHA/hydroxypropylacrylamide)

AHA (10 g), hydroxypropylacrylamide (10 g), methylenebisacrylamide (2.2 g), and AIBN (0.25 g) were suspended in DMSO (50 mL) under a nitrogen atmosphere. The mixture was slowly heated. At 39° C. the mixture was homogeneous. The solution gelled just below 60° C. The heat of polymerization took the temperature up to 115° C. The solution was allowed to slowly cool to room temperature under a nitrogen atmosphere and allowed to sit for 3 hours. The gel was removed, blended twice with isopropanol, and the solid was collected by filtration. The solid was rinsed three times in water, three times in isopropanol, and dried in a vacuum oven to yield 15.5 g.

48. Copoly(AHA/dodecylacrylamide)

AHA (4 g), dodecylacrylamide (4 g), methylenebisacrylamide (0.9 g), and 0.25 g AIBN were dissolved in dimethylsulfoxide (25 mL). The mixture was slowly heated under a nitrogen atmosphere. Before reaching 90° C. the solution began to polymerize, driving the temperature up to 110° C. The solution was allowed to cool and sit overnight under nitrogen. The solid was removed, blended with isopropanol (500 mL), and collected by filtration. The solid was resuspended and then filtered from isopropanol once, from water three times, and finally from isopropanol three times. The solid was dried in a vacuum oven to yield 5.3 g.

49. Copoly(AHA/acrylamide/vinylphosphonic acid)

AHA (5 g), acrylamide (5 g), vinylphosphonic acid (5.9 g of 90% solution), methylenebisacrylamide (1.5 g), and AIBN (0.35 g) were dissolved in dimethylsulfoxide (35 mL). The mixture was slowly heated under a nitrogen atmosphere. At 50° C. the solution gelled, with the heat of polymerization heating it to 110° C. The gel was allowed to cool and sit for 4 hours under nitrogen. The solid was removed, blended three times with methanol, three times with water, three times with isopropanol, and dried in a vacuum oven to yield 9.2 g.

50. N-Dehydroabeitylacrylamide

Dehydroabeitylamine (15 g of Technical Grade) and triethylamine (5.85 g) dissolved in THF (100 mL) was added dropwise to acryloyl chloride (5.25 g) dissolved in THF (100 mL) in an ice bath. The white solid (triethylaminehydrochloride) was filtered off and discarded. The solvent was evaporated in vacuo to leave an oil. The oil was dissolved in ethylacetate (300 mL), rinsed once with water (500 mL) saturated with NaCl (whose pH became 2.3), rinsed once with 5% NaHCO$_3$ saturated with NaCl (200 mL; pH became 7.8), and finally was dried over MgSO$_4$ before evaporation of the ethylacetate in vacuo to leave 16 g of solid.

51. Copoly(ARA/dehydroabeitylacrylamide/acrylamide)

ARA (3 g), N-dehydroabeitylacrylamide (3 g), acrylamide (3 g), methylenebisacrylamide (1.0 g) and AIBN (0.25 g) were dissolved in dimethylsulfoxide (25 mL). The mixture was slowly heated under a nitrogen atmosphere. Below 90° C. the solution gelled, with the heat of polymerization heating it to 115° C. The gel was allowed to cool under nitrogen. The solid was removed, blended three times with isopropanol (500 mL), twice with water (1 L), three times with methanol, and dried in a vacuum oven to yield 6.5 g.

52. N-Methyl-N-β-cyanoethylacrylamide

N-Methyl-N-β-cyanoethylacrylamide (N-Methyl-β-alaninenitrile; 30 g) and triethylamine (36.4 g) were dissolved in THF (100 mL). This solution was added dropwise to acryloyl chloride (32.6 g) dissolved in THF (200 mL) in an ice bath. The solid was filtered off and the solvent removed in vacuo to leave 37.8 g.

53. Poly(N-Methyl-N-β-cyanoethylacrylamide)

N,N-Methylcyanoethylacrylamide (10 g), methylenebisacrylamide (1.1 g), and AIBN (0.3 g) were dissolved in dimethylsulfoxide (50 mL). The mixture was slowly heated under a nitrogen atmosphere. At ~100° C. the solution polymerized, sending the temperature up to 115° C. The solution was allowed to cool and sit overnight. The gel was removed, blended gently four times in isopropanol, and dried in a vacuum oven to yield 10.65 g.

54. Cystaminediacrylamide

Cystamine dihydrochloride (20 g) and potassium carbonate (61.4 g) were dissolved in water (150 mL) and placed in an ice bath. Acryloyl chloride (24.2 g) was added dropwise, with solid formation on addition. The solid was filtered off, rinsed twice with water, and dried in a vacuum oven to yield 16.6 g.

55. Poly(cystaminediacrylamide

Cystaminediacrylamide (15 g) and methylenebisacrylamide (1.65 g) were dissolved in a mixture of methanol (150 mL) and water (50 mL). The mixture was heated to reflux allowing near complete dissolution of the solid. Potassium persulfate (0.3 g) and potassium metabisulfite (0.3 g) were each dissolved in water (2–3 mL). After dissolving they were mixed together and within a few seconds added to the hot monomer solution. Polymer formation was evident within 1 minute. The solution was refluxed for 1 hour, cooled to room temperature, and the solid was filtered off. The solid was rinsed twice in water, twice in methanol, twice in isopropanol, and dried in a vacuum oven to yield 7.0 g.

56. Poly(mercaptoethylacrylamide)

Method A

Poly(cystaminediacrylamide) (0.8 g; ground and sieved to −80/+200 mesh size) was suspended in a mixture of methanol (75 mL), water (50 mL), and mercaptoethanol (10 mL). The mixture was stirred overnight under a nitrogen atmosphere. The solid was filtered off, rinsed four times in methanol, three times in isopropanol, and dried in a vacuum oven to yield 0.65 g of pink solid.

Method B

Poly(cystaminediacrylamide) (1.25 g; unsieved) was suspended in water (100 mL). Sodium borohydride (2.25 g) was added under a nitrogen atmosphere. The solution was stirred overnight and the solid was filtered off, rinsed three times in water, three times in methanol, and dried in a vacuum oven to yield 0.84 g of pink solid.

57. Poly(itaconic anhydride)

Itaconic anhydride (22.4 g), ethyleneglycoldimethacrylate (13.3 g), and toluene (500 mL) were mixed in a 1 L flask and heated to 80° C. Azobisisobutryonitrile (2 g) was dissolved in toluene (50 mL) and added dropwise over a two hour period to the monomer solution. The solution was stirred for one additional hour at 80° C., cooled to room temperature, and the solid polymer was filtered off. The solid was rinsed with THF, stirred in THF for 30 minutes followed by filtration, and dried in a vacuum oven to yield 37 g.

58. Poly(aminoethylpiperazine itaconate)

Poly(itaconic anhydride) (5 g) was suspended in acetone (100 mL) to which was added 1-(2-aminoethyl)piperazine (26 g). The solution was stirred for 1 hour and the solids were filtered off, rinsed twice in acetone, once in water, and suspended in water (150 mL) where the pH was read to be 7.2. The solids were again filtered off, rinsed once in water, once in 1N HCl (pH of the slurry=0.75), and twice in water (pH <3 for both). The solids were suspended in water (300 mL) and 1N NaOH was added to pH 7.0. The solids were rinsed three additional times in water, three times in methanol, once in isopropanol, and dried in a vacuum oven to yield 5.8 g.

59. N-Imidazolepropylacrylamide 1-(3-aminopropyl)imidazole (25 g) dissolved in THF (100 mL) was added dropwise to acryloyl chloride (18.1 g) dissolved in THF (200 mL) in an ice bath. The solid was formed was filtered off and dried in a vacuum oven to yield 39.2 g of a semisolid. This crude material was polymerized without further purification.

60. Poly(N-imidazolepropylacrylamide)

Crude N-imidazolepropylacrylamide (17.7 g) and methylenebisacrylamide (2.0 g) were dissolved in water (100 mL). Potassium persulfate (0.4 g) and potassium metabisulfite (0.4 g) were each dissolved in water (3 mL). After dissolving they were mixed together and within a few seconds added to the monomer solution under a nitrogen atmosphere. In ~10 minutes the solution gelled lightly and was left overnight. The gel was blended four times with isopropanol (500 mL) and dried in a vacuum oven to yield 11.8 g. The solid was resuspended in water (500 mL), stirred 30 minutes, and refiltered twice more. The solid was rinsed twice in methanol, three times in isopropanol, and dried in a vacuum oven to yield 6.7 g.

61. Cysteinediacrylamide

Cysteine (50 g) and potassium carbonate (174 g) were nearly dissolved in water (400 mL) and placed in an ice bath. Acryloyl chloride (57 g) was added dropwise over a 1 hour period, keeping the temperature below 15° C. The mixture was allowed to warm to room temperature and the pH was measured to be 7.9. Concentrated HCl was added until the pH reached 1.2. The water was removed in vacuo and THF (500 mL) was added and stirred for 20 minutes. The solid was filtered off and discarded. The THF was removed in vacuo to leave a thick liquid. The liquid was suspended in acetone (1 L) and stirred for 30 minutes. Any solid remaining was filtered off and discarded. The acetone was removed in vacuo to yield 78.3 g.

62. Poly(cysteinediacrylamide)

Cysteineacrylamide (75.5 g) and methylenebisacrylamide (7 g) were dissolved in a mixture containing water (300 mL) and methanol (200 mL). Potassium persulfate (1.0 g) and potassium metabisulfite (1.0 g) were each added with stirring. No change was observed in 15 minutes. The addition of initiators was repeated dissolving each in a few mL of water prior to addition. No sign of polymerization was observed. AIBN (1.0 g) was added and the solution heated to reflux under a nitrogen atmosphere. Before reaching reflux a copious white solid was formed. The heating was stopped and the water (2 L) and stirred 1 hour. The solids were collected by filtration, resuspended in methanol (2 L), filtered off, and dried in a vacuum oven to yield 76.7 g.

63. Poly(AEABMP)

Poly(AEA) (19.12 g); made without any water washes) was suspended in methanol (100 mL). A second solution containing KOH (7.2 g) and methanol (25 mL) was partially added (~1/3) until the apparent pH stabilized at 9. Water (200 mL) was added, and additional KOH/methanol solution was added until the pH reached 12. After stirring the mixture overnight the solid was filtered off, rinsed with water, suspended in water (300 mL), stirred 1 hour, filtered off, and dried in a vacuum oven to yield 11.2 g of deprotonated poly (AEA).

This solid (11.2 g) was placed in a 250 mL flask containing methanol (75 mL). Methyl acrylate (25.8 g) was added and the mixture stirred for 21 days. The solid was then filtered off and dried in a vacuum oven to yield 20.2 g.

64. Poly(AEABPHA)

Hydroxylamine hydrochloride (22.2 g) was dissolved in methanol (110 mL) in a 500 mL flask. A solution containing KOH (30.7 g) and methanol (70 mL) was added and the solution cooled to 28° C. after a slight exotherm to 52° C. The cooled solution was filtered, the solid washed with methanol, and the liquid fraction combined with poly (AEABMP) (20.2 g). After stirring the mixture for 4 days, acetic acid (30 g) was added and the mixture stirred for 1 hour. The solid was filtered off, rinsed with water, resuspended in water, stirred 1 hour and finally filtered off. The solid was dried in a vacuum oven to yield 9.55 g.

65. Poly(methacrylamidopropyltrimethylammonium chloride)

Methacrylamidopropyltrimethylammonium chloride (38 mL of 50% aqueous solution) and methylenebismethacrylamide (2.2 g) were stirred in a beaker at room temperature. Methanol (10 mL) was added and the solution was warmed to 40° C. to fully dissolve the bisacrylamide. Potassium persulfate (0.4 g) was added and the solution stirred for 2 minutes. Potassium metabisulfite (0.4 g) was added and stirring was continued. After 5 minutes the solution was put under a nitrogen atmosphere. After 20 minutes the solution contained significant precipitate and the solution was allowed to sit overnight. The solid was washed three times with isopropanol and collected by filtration. The solid was then suspended in water (500 mL) and stirred for several hours before being collected by centrifugation. The solid was again washed with water and collected by filtration. The solid was then dried in a vacuum oven to yield 21.96 g.

66. Poly(methacryloyl chloride)

Methacryloyl chloride (20 mL), divinylbenzene (4 mL of 80% purity), AIBN (0.4 g) and THF (150 mL) were stirred at 60° C. under a nitrogen atmosphere for 18 hours. The solution was cooled and the solid was filtered off, rinsed in THF, then acetone, and dried in a vacuum oven to yield 8.1 g.

67. Poly(salicylic acrylamide)

4-Aminosalicylic acid (10 g), triethylamine (2 mL), acetone (50 mL) and poly(methacryloyl chloride) (0.88 g) were stirred together for 18 hours. The solid was filtered off, rinsed with water, stirred in water (500 mL) for 30 minutes, filtered of, stirred in water a second time, stirred in isopropanol, and dried in a vacuum oven to yield 0.84 g.

68. Poly(3-hydroxytyracrylamide)

3-Hydroxytyramine hydrochloride (2.0 g), triethylamine (5 mL), acetone (100 mL) and poly(methacryloyl chloride) (1.0 g) were stirred together for 4 days. Water (100 mL) was added and the solution stirred 30 minutes. The solid was filtered off, rinsed with water, stirred in water (500 mL) for 30 minutes, filtered off, stirred in two more times, stirred in methanol (500 mL) three times, and dried in a vacuum oven to yield 1.12 g.

69. Poly(N-methyl-N-hydroxymethacrylamide)

Methylhydroxylamine hydrochloride (8.25 g), poly (methacryloyl chloride) (5.0 g), and 1M NaOH (100 mL) were mixed together and the pH adjusted to 7.7 with 1M HCl. The mixture was blended for 3 minutes at high speed in a blender and then stirred for 18 hours. The solid was filtered off, stirred in water (500 mL) for 10 minutes, filtered off, rinsed twice in water, once in isopropanol, and dried in a vacuum oven to yield 4.5 g.

70. NHS-acrylate

N-Hydroxysuccinimide (NHS, 157.5 g) was dissolved in chloroform (2300 mL) in a 5 L flask. The solution was cooled to 0° C. and acryloyl chloride (132 g) was added dropwise, keeping T<2° C. After addition was completed, the solution was stirred for 1.5 hours, rinsed with water (1100 mL) in a separatory funnel and dried over anhydrous sodium sulfate. The solvent was removed under vacuum and a small amount of ethyl acetate was added to the residue. This mixture was poured into hexane (200 mL) with stirring. The solution was heated to reflux, adding more ethyl acetate (400 mL). The insoluble NHS was filtered off, hexane (1 L) was added, the solution was heated to reflux, ethyl acetate (400 mL) was added, and the solution allowed to cool to <10° C. The solid was then filtered off and dried in a vacuum oven to yield 125.9 g. A second crop of 80 g was subsequently collected by further cooling.

71. Poly(NHS-acrylate)

NHS-acrylate (28.5 g), methylenebisacrylamide (1.5 g) and tetrahydrofuran (500 mL) were mixed in a 1 L flask and heated to 50° C. under a nitrogen atmosphere. Azobisisobutyronitrile (0.2 g) was added, the solution was stirred for 1 hour, filtered to remove excess N-hydroxysuccinimide, and heated to 50° C. for 4.5 hours under a nitrogen atmosphere. The solution was then cooled and the solid was filtered off, rinsed in tetrahydrofuran, and dried in a vacuum oven to yield 16.1 g.

72. Poly(PEH-acrylamide)

Poly(NHS-acrylate) (5.0 g) was suspended in a solution containing water (100 mL) and pentaethylene hexamine (30 mL) which had been adjusted to pH 10 with concentrated HCl. After four days of stirring, the solid was filtered off and resuspended in water (500 mL). The mixture was stirred for 4 hours, the solid was filtered off, and the wash repeated. The solid was then rinsed briefly with water twice, isopropanol once, and dried in a vacuum oven to yield 4.7 g.

73. Poly(TAEA-acrylamide)

Poly(NHS-acrylate) (4.4 g) was suspended in a solution containing water (100 mL) and tris(2-aminoethyl)amine (30 mL) which had been adjusted to pH 9 with concentrated HCl. After four days of stirring, the solid was filtered off and resuspended in water (500 mL). The mixture was stirred for 4 hours, the solid was filtered off, and the wash repeated. The solid was then rinsed briefly with water twice, isopropanol once, and dried in a vacuum oven to yield 3.4 g.

74. Poly(cholinevinylphosphonate)

Vinylphosphonic acid (52.3 g) and methylenebisacrylamide (5.2 g) were mixed, heated gently to dissolve, sealed in a glass reaction kettle under vacuum, and exposed to uv light for 3 days. The resulting solid was removed, blended twice in isopropanol (600 mL), collected by filtration, and dried in a vacuum oven yielding 25.4 g. This solid was then ground and suspended in water (400 mL). Choline bicarbonate was added until the pH reached 6.5. The solution was stirred for 1 hour, after which the solid was filtered off with the addition of ethanol to collapse the gel. The solid was rinsed twice with ethanol (500 mL) and dried in a vacuum oven to yield 23.8 g.

75. Poly(allylamine hydrochloride)

To a 5 L, water jacketed reaction kettle equipped with 1) a condenser topped with a nitrogen gas inlet and 2) a thermometer and 3) a mechanical stirrer was added concentrated hydrochloric acid (2590 mL). The acid was cooled to 5° C. using circulating water in the jacket of the reaction kettle at 0° C. Allylamine (2362 mL; 1798 g) was added dropwise with stirring, maintaining a temperature of 5°–10° C. After the addition was complete, 1338 mL of liquid was removed by vacuum distillation at 60°–70° C. Azobis(amidinopropane)dihydrochloride (36 g) suspended in 81 mL water was added. The kettle was heated to 50° C. under a nitrogen atmosphere with stirring for 24 hours. Azobis(amidinopropane)dihydrochloride (36 g) suspended in 81 mL water was again added and the heating and stirring continued for an additional 44 hours. Distilled water (720 mL) was added and the solution allowed to cool with stirring. The liquid was added dropwise to a stirring solution of methanol (30 L). The solid was then removed by filtration, resuspended in methanol (30 L), stirred 1 hour, and collected by filtration. This methanol rinse was repeated once more and the solid was dried in a vacuum oven to yield 2691 g of a granular white solid poly(allylamine hydrochloride).

76. Poly(allylamine/epichlorohydrin)

To a 5 gallon bucket was added poly(allylamine hydrochloride) (2.5 kg) and water 10 L). The mixture was stirred to dissolve and the pH was adjusted to 10 with a solid NaOH. The solution was allowed to cool to room temperature in the bucket and epichlorohydrin (250 mL) was added all at once with stirring. The mixture was stirred gently until it gelled after about 15 minutes. The gel was allowed to continue curing for 18 hours at room temperature. The gel was then removed and put into a blender with isopropanol (about 7.5 L). The gel was mixed in the blender with about 500 mL isopropanol for ~3 minutes to form coarse particles and the solid was then collected by filtration. The solid was rinsed three times by suspending it in 9 gallons of water, stirring the mixture for 1 hour, and collecting the solid by filtration. The solid was rinsed once by suspending it in isopropanol (60 L), stirring the mixture for 1 hour, and collecting the solid by filtration. The solid was dried in a vacuum oven for 18 hours to yield 1.55 Kg of a granular, brittle, white solid.

77. Poly(allylamine/butanedioldiglycidyl ether)

To a 5 gallon plastic bucket was added poly(allylamine hydrochloride) (500 g) and water (2 L). The mixture was stirred to dissolve and the pH was adjusted to 10 with solid NaOH (142.3 g). The solution was allowed to cool to room temperature in the bucket and 1,4-butanedioldiglycidyl ether (130 mL) was added all at once with stirring. The mixture was stirred gently until it gelled after 4 minutes. The gel was allowed to continue curing for 18 hours at room temperature. The gel was then removed and dried in a vacuum oven at 75° C. for 24 hours. The dry solid was ground and sieved for ~30 mesh and then suspended in 6 gallons of water. After stirring for 1 hour the solid was filtered off and rinse process repeated twice more. The solid was rinsed twice in isopropanol (3 gallons), and dried in a vacuum oven at 50° C. for 24 hours to yield 580 g of a white solid.

78. Poly(allylamine/ethanedioldiglycidyl ether)

To a 100 mL beaker was added poly(allylamine hydrochloride) (10 g) and water (40 mL). The mixture was stirred to dissolve and the pH was adjusted to 10 with solid NaOH. The solution was allowed to cool to room temperature in the beaker and 1,2 ethanedioldiglycidyl ether (2.0 mL) was added all at once with stirring. The mixture was allowed to continue curing for 18 hours at room temperature. The gel was then removed and blended in 500 mL of methanol. The solid was filtered off and suspended in water (500 mL). After stirring for 1 hour the solid was filtered off and the rising process repeated. The solid was rinsed twice in isopropanol (400 mL), and dried in a vacuum oven at 50° C. for 24 hours to yield 8.7 g of a white solid.

79. Poly(allylamine/dimethylsuccinate)

To a 500 mL round bottom flask was added poly(allylamine hydrochloride) (10 g), methanol (100 mL), and triethylamine (10 mL). The mixture was stirred and dimethylsuccinate (1 mL) was added. The solution was heated to reflux and stirring turned off after 30 minutes. After 18 hours the solution was cooled to room temperature and solid was filtered off and suspended in water (1 L). After stirring for 1 hour the solid was filtered off and the rinse process repeated twice more. The solid was rinsed once in isopropanol (800 mL), and dried in a vacuum oven at 50° C. for 24 hours to yield 5.9 g of a white solid.

80. Poly(allyltrimethylammonium chloride)

To a 500 mL three necked flask equipped with a magnetic stirrer, a thermometer, and a condenser topped with a nitrogen inlet, was added poly(allylamine) crosslinked with epichlorohydrin (5.0 g), methanol (300 mL), methyl iodide (20 mL), and sodium carbonate (50 g). The mixture was then cooled and water was added to total volume of 2 L. Concentrated hydrochloric acid was added until no further bubbling resulted and the remaining solid was filtered off. The solid was rinsed twice in 10% aqueous NaCl (1 L) by stirring for 1 hour followed by filtration to recover the solid. The solid was then rinsed three times by suspending it in water (2 L), stirring for 1 hour, and filtering to recover the solid. Finally, the solid was rinsed as above in methanol and dried in a vacuum over at 50° C. for 18 hours to yield 7.7 g of white granular solid.

81. Preparation of a Poly(allylamine)Hydrochloride

To a 2 liter, water-jacketed reaction kettle equipped with (1) a condenser topped with a nitrogen gas inlet, (2) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 grams) was added dropwise with stirring while maintaining the reaction temperature at 5°–10° C. After addition was complete, the mixture was removed, placed in a 3 liter one-neck flask, and 206 grams of liquid was removed by rotary vacuum evaporation at 60° C. Water (20 mL) was then added and the liquid was returned to the reaction kettle. Azobis(amidinopropane)dihydrochloride (0.5 grams) suspended in 11 mL of water was then added. The resulting reaction mixture was heated to 50° C. under a nitrogen atmosphere with stirring for 24 hours. Additional azobis(amidinopropane)dihydrochloride (0.5 grams) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, re-suspended in methanol (4 L), stirred for 1 hour, and collected by filtration. The methanol rinse was then repeated one more time and the solid dried in a vacuum oven to afford 215.1 grams of poly(allylamine)hydrochloride as a granular white solid.

82. Preparation of Poly(allylamine)Hydrochloride Crosslinked With Epichlorohydrin To a 5 gallon vessel was added poly(allylamine) hydrochloride prepared as described in Example 81 (1 kg) and water (4 L). The mixture was stirred to dissolve the hydrochloride and the pH was adjusted by adding solid NaOH (284 grams). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum over at 50° C. for 18 hours to yield about 677 grams of the crosslinked polymer as a granular, brittle, white solid.

83. Alkylation of Six Percent Crosslinked Amine Polymer

Crosslinked poly(allylamine) was made as stated in Example 82. To a large flask were added the crosslinked poly(allylamine) (300 grams; ground to ~30 mesh), (6-bromohexyl)trimethylammonium bromide (316.4 grams), 1-bromodecane (188.9 grams), and methanol (8 L). The mixture was heated to 65° C. with stirring. Upon reaching 65° C. (~40 minutes), aqueous sodium hydroxide (44.9 grams of 50% solution) was added and the stirring continued at 65° C. for 2 hours. Two additional aliquots of aqueous sodium hydroxide (44.9 grams of 50% solution each) were sequentially added and the stirring continued at 65° C. for an additional 2 hours for each aliquot. A final aliquot of aqueous sodium hydroxide (44.9 grams of 50% solution) was then added and the stirring continued at 65° C. for an additional 12 hours. The mixture was then allowed to cool to room temperature (~4 hours).

The solid product was filtered off and resuspended in methanol such that the conductivity was less than 2.5 mS/cm (~20 L). The mixture was stirred for 30 minutes and the solid filtered off. The solid was then washed by suspension, stirring for 30 minutes, and filtration, from the following fluids:

1. 11 L 2M NaCl (aqueous)
2. 11 L 2M NaCl (aqueous)
3. 8 L deionized water
4. 8 L deionized water
5. 8 L deionized water The solid was then dried in a 60° C. forced air drying oven to yield 450 grams of an off-white solid. The solid was then ground and passed through an 80 mesh sieve.

84. Alkylation of Crosslinked Amine Polymer

The procedure for crosslinked amine polymer, in Example 83, was repeated using different amounts of reagents. All amounts, times and procedures were unchanged except:

570 grams (6-bromohexyl)trimethylammonium bromide
390 grams 1-bromodecane
80.1 grams aqueous sodium hydroxide in each addition
16.5 L 2M NaCl (aqueous) in each wash
9 L deionized water in each wash The yield of this reaction was: 684.6 grams of an off-white solid.

85. Alkylation of Three Percent Crosslinked Amine Polymer

Crosslinked poly(allylamine) was made by the same method described in Example 82 except that the level of epichlorohydrin was 25 mL instead of 50 mL, resulting in 3% crosslinked poly(alkylamine). The procedure of Example 3 was then repeated using different amounts of reagents. All amounts, times, and procedures were unchanged except:

300 grams of Poly(allylamine) crosslinked at 3%, -30 mesh size
636 grams (6-bromohexyl)trimethylammonium bromide
435 grams 1-bromodecane
88.7 grams aqueous sodium hydroxide in each addition
18.4 L 2M NaCl (aqueous) in each wash
10 L deionized water in each wash 86. Alkylation of Six Percent Crosslinked Poly(allylamine) with (6-bromohexyl)Tri-methylammonium Bromide and 1-Bromodecane To a 12-L round bottom flask equipped with a mechanical stirrer, a thermometer, and a condenser was added methanol (5 L) and sodium hydroxide (133.7 grams). The mixture was stirred until the solid was dissolved and 6 percent crosslinked poly(allylamine) (from Example 81; 297 grams; ground to -80 mesh size) was added along with additional methanol (3 L). (6-Bromohexyl)trimethylammonium bromide (522.1 grams) and 1-bromodecane (311.7 grams) were added and the mixture heated to 65° C. with stirring. After 18 hours at 65° C. the mixture was allowed to cool to room temperature. The solid was filtered off and rinsed by suspending, stirring for 30 minutes, and filtering off the solid from:

1. Methanol, 12 L
2. Methanol, 12 L
3. 2M Aqueous NaCl 22 L
4. 2M Aqueous NaCl 22 L
5. Deionized Water 22 L
6. Deionized Water 22 L
7. Deionized Water 22 L
8. Isopropanol 22 L The solid was dried in a vacuum oven at 50° C. to yield 505.1 grams of off-white solid. The solid was then ground to pass through an 80 mesh sieve.

87. Alkylation of Six Percent Crosslinked Poly(allylamine) with (3-Bromopropyl)dodecyldimethylammomium Bromide A. Six percent crosslinked poly(allylamine) was made as stated in Example 82. To a flask were added the crosslinked poly(allylamine) (12.5 grams; 6% crosslinked; ground to ~30 mesh), (3-bromopropyl)dodecyldimethylammonium bromide (17.5 grams; made by reaction of 1,3-dibromopropane and N,N-dimethyl-1-aminododecane in diethyl ether), and methanol (334 mL). The mixture was heated to 65° C. with stirring. Upon reaching 65° C., aqueous sodium hydroxide (1.14 grams of 50% solution) was added and the stirring continued at 65° C. for 2 hours. Two additional aliquots of aqueous sodium hydroxide (1.14 grams of 50% solution) were sequentially added and the stirring continued at 65° C. for an additional 2 hours for each aliquot. Aqueous sodium hydroxide (1.14 grams of 50% solution) was then added and the stirring continued at 65° C. for an additional 12 hours. The mixture was then allowed to cool to room temperature.

The solid product was filtered off and washed by suspension, stirring for 30 minutes, and filtration, from the following fluids:

459 mL 2M NaCl (aqueous)
2. 459 mL 2M NaCl (aqueous)
3. 2 L deionized water
4. 2 L deionized water
5. 2 L deionized water
6. 2 L deionized water The solid was then dried in a 60° C. forced-air oven to yield 17.4 grams of an off-white solid. The solid was then ground and passed through an 80 mesh sieve.

B. Six percent crosslinked poly(allylamine) was made as stated in Example 82. To a flask were added the crosslinked poly(allylamine) (12.5 grams; 6% crosslinked; ground to ~30 mesh), (3-bromopropyl)dodecyldimethylammonium bromide (35 grams; made by reaction of 1,3-dibromopropane and N,N-dimethyl-1-aminododecane in diethyl ether), and methanol (334 mL). The mixture was heated to 65° C. with stirring. Upon reaching 65° C., aqueous sodium hydroxide (1.99 grams of 50% solution) was added and the stirring continued at 65° C. for 2 hours. Two additional aliquots of aqueous sodium hydroxide (1.99 grams of 50% solution) were sequentially added and the stirring continued at 65° C. for an additional 2 hours for each aliquot. Aqueous sodium hydroxide (1.99 grams of 50% solution) was then added and the stirring continued at 65° C. for an additional 12 hours. The mixture was then allowed to cool to room temperature.

The solid product was filtered off and washed by suspension, stirring for 30 minutes, and filtration, from the following fluids:

1. 459 mL 2M NaCl (aqueous)
2. 459 mL 2M NaCl (aqueous)
3. 2 L deionized water
4. 2 L deionized water
5. 2 L deionized water
6. 2 L deionized water The solid was then dried in a 60° C. forced air drying oven to yield 25.6 grams of an off-white solid. The solid was ground and passed through an 80 mesh sieve.

C. Crosslinked poly(allylamine) was produced by the method of Example 82, with the exception that 16.7 mL of epichlorohydrin was employed, rather than 50 mL. To a flask were added crosslinked poly(allylamine) (12.5 grams; 2% crosslinked; ground to ~30 mesh), (3-bromopropyl) dodecyldimethylammonium bromide (140.8 grams; made by reaction of 1,3-dibromopropane and N,N-dimethyl-1-aminododecane in diethyl ether), and methanol (334 mL). The mixture was heated to 65° C. with stirring. Upon reaching 65° C., aqueous sodium hydroxide (7.1 grams of 50% solution) was added and the stirring continued at 65° C. for 2 hours. Two additional aliquots of aqueous sodium hydroxide (7.1 grams of 50% solution) were sequentially added and the stirring continued at 65° C. for an additional 2 hours for each aliquot. Aqueous sodium hydroxide (7.1 grams of 50% solution) was added and the stirring continued at 65° C. for an additional 12 hours. The mixture was then allowed to cool to room temperature.

The solid product was filtered off and washed by suspension, stirring for 30 minutes, and filtration from the following fluids:

1. 1.7 L 2M NaCl (aqueous)
2. 1.7 L 2M NaCl (aqueous)
3. 8 L deionized water
4. 8 L deionized water
5. 8 L deionized water
6. 8 L deionized water
7. 4 L deionized water The solid was then dried in a 60° C. forced air drying oven to yield 39.8 grams of an off-white solid. The solid was ground and passed through an 80 mesh sieve.

88. Alkylation of Six Percent Crosslinked Poly(allylamine) with (3-bromopropyl)octyldimethylammonium Bromide Six percent crosslinked poly(allylamine) was made as stated in Example 82. To a flask were added crosslinked poly(allylamine) (12.5 grams; 6% crosslinked; ground to ~30 mesh), (3-bromopropyl)octyldimethylammonium bromide (30.2 grams; made by reaction of 1,3-dibromopropane and N,N-dimethyl-1-aminooctane in diethyl ether), and methanol (334 mL). The mixture was heated to 65° C. with stirring. Upon reaching 65° C. aqueous sodium hydroxide (2.0 grams of 50% solution) was added and the stirring continued at 65° C. for 2 hours. Two additional aliquots of aqueous sodium hydroxide (2.0 grams of 50% solution) were sequentially added and the stirring continued at 65° C. for an additional 2 hours for each aliquot. Aqueous sodium hydroxide (2.0 grams of 50% solution) was then added and the stirring continued at 65° C. for an additional 12 hours. The mixture was then allowed to cool to room temperature.

The solid product was filtered off and washed by suspension, stirring for 30 minutes, and filtration from the following fluids:

1. 800 mL 2M NaCl (aqueous)
2. 800 mL 2M NaCl (aqueous)
3. 2 L deionized water
4. 2 L deionized water
5. 1 L deionized water The solid was then dried in a 60° C. forced air drying oven to yield 16.8 grams of an off-white solid. The solid was ground and passed through an 80 mesh sieve.

89. Alkylation of Six Percent Crosslinked Poly(allylamine) with (6-bromohexyl)octyldimethylammonium Bromide Six percent crosslinked poly(allylamine) was made as stated in Example 82. To a flask were added crosslinked poly(allylamine) (12.5 grams; 6% crosslinked; ground to ~30 mesh), (6-bromohexyl)octyldimethylammonium bromide (33.7 grams; made by reaction of 1,6-dibromohexane and N,N-dimethyl-1-aminooctane in diethyl ether), and methanol (334 mL). The mixture was heated to 65° C. with stirring. Upon reaching 65° C., aqueous sodium hydroxide (1.68 grams of 50% solution) was added and the stirring continued at 65° C. for 2 hours. Two additional aliquots of aqueous sodium hydroxide (1.68 grams of 50% solution) were sequentially added and the stirring continued at 65° C. for an additional 2 hours for each aliquot. Aqueous sodium hydroxide (1.68 grams of 50% solution) was added and the stirring continued at 65° C. for an additional 12 hours. The mixture was then allowed to cool to room temperature.

The solid product was filtered off and washed by suspension, stirring for 30 minutes, and filtration from the following fluids:

1. 1 L 2M NaCl (aqueous)
2. 1 L 2M NaCl (aqueous)
3. 1 L deionized water repeated until solution conductivity is less than 1 mS/cm The solid was then dried in a 60° C. forced air drying oven to yield 15.7 grams of an off-white solid. The solid was ground and passed through an 80 mesh sieve.

Use

The polymers of the invention are intended to decrease the uptake of dietary iron, after oral administration. The polymers may be administered as a composition which includes ingredients, such as other therapeutically active substances, inert ingredients, and carrier compounds. The components of the composition must be compatible, meaning that the components must be capable of being commingled with the polymer and with each other in a manner such that there is no interaction which would substantially reduce during use the composition's efficacy for decreasing the absorption of dietary iron.

The composition formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container.

The term "patient" used herein is taken to mean any mammalian patient to which iron-binding polymers may be administered. Patients specifically intended for treatment with the method of the invention include humans, as well as nonhuman primates, sheep, horses, cattle, goats, pigs, dogs, cats, rabbits, guinea pigs, hamsters, gerbils, rats and mice.

The polymers would be taken orally, and would then mix with the dietary constituents in the digestive track and inhibit absorption of iron. The polymers would be acting by binding the iron and reducing its bioavailability. The polymers are preferably crosslinked to form small particles that are confined to the digestive track and would not be available to the blood or other extraliminal fluids or organs. As the dietary constituents passed through the individual, so too would the polymer, until eventually it was excreted in the feces.

In order to prevent dietary uptake one must prevent both free iron and heme-bound iron from entering the mucosal cells. To do this, in one embodiment the therapeutic polymer would be administered to remove from 70–95% of the available dietary iron, leaving a small but adequate amount of iron available to meet the minimal ongoing iron needs of patients, as well as the iron requirements of the patients' intestinal flora. Alternatively, enough polymer may be administered to sequester all (99+%) of the dietary iron, and the patient would also take an iron supplement at a time when no sequesterant is present. This latter approach would allow better control since it may be difficult for patients to balance their sequesterant dose with their dietary iron intake to leave an appropriate amount of non-sequestered iron.

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for removing iron from a patient comprising orally administering to said patient a therapeutically effective amount of a composition comprising at least one hydrophilic cross-linked aliphatic amine polymer.

2. A method for removing iron from a patient as claimed in claim 1, comprising at least one polymer characterized by a repeat unit having the formula

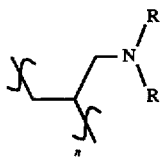

or a copolymer thereof, wherein n is an integer and each R, independently, is H or a substituted or unsubstituted alkyl, alkylamino, or aryl group.

3. The method of claim 2 wherein said polymer is crosslinked with a crosslinking agent wherein said crosslinking agent is present in said composition from about 0.5% to about 75% by weight.

4. The method of claim 3 wherein said crosslinking agent is epichlorohydrin.

5. A method for removing iron from a patient as claimed in claim 1 comprising at least one polymer characterized by a repeat unit having the formula

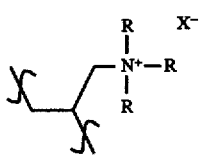

or a copolymer thereof, wherein each n is an integer, each R, independently, is H or a substituted or unsubstituted alkyl, alkylamino, or aryl group.

6. The method of claim 5 wherein said polymer is crosslinked with a crosslinking agent, wherein said agent is present in said composition from about 0.5% to about 75% by weight.

7. The method of claim 6, wherein said crosslinking agent is epichlorohychin.

8. A method for removing iron from a patient as claimed in claim 1 comprising at least one polymer characterized by a repeat unit having the formula

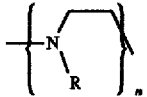

or a copolymer thereof, wherein n is an integer, each R, independently, is H or a substituted or unsubstituted alkyl, alkylamino, or aryl group.

9. The method of claim 8 wherein said polymer is crosslinked with a crosslinking agent, wherein said agent is present in said composition from about 0.5% to about 75% by weight.

10. The method of claim 9, wherein said crosslinking agent is epichlorohydrin.

11. The method of claim 8 wherein the polymer is a copolymer comprising a second repeat unit having the formula

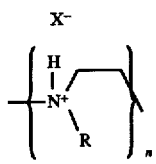

wherein each n, independently, is an integer and R is a substituted or unsubstituted alkyl, alkylamino, or aryl group.

12. A method for removing iron from a patient as claimed in claim 1 comprising at least one polymer characterized by a repeat unit having the formula

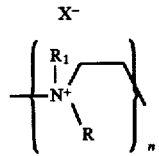

or a copolymer thereof, wherein n is an integer, and each $R_1$ and $R_2$, independently, is H or a substituted or unsubstituted alkyl, alkylamino, or aryl group, each $X^-$ is an exchangeable negatively charged counterion.

13. The method of claim 12 wherein said polymer is crosslinked with a crosslinking agent, wherein said agent is present in said composition from about 0.5% to about 75% by weight.

14. The method of claim 13, wherein said crosslinking agent is epichlorohydrin.

15. A method for removing iron from a patient as claimed in claim 1 comprising at least one polymer characterized by a repeat unit having the formula

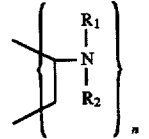

or a copolymer thereof, wherein n is an integer, each $R_1$ and $R_2$, independently, is H, a substituted or unsubstituted alkyl, alkylamino or aryl group containing 1 to 20 carbon atoms.

16. The method of claim 13 wherein said polymer is crosslinked with a crosslinking agent, wherein said agent is present in said composition from about 0.5% to about 75% by weight.

17. The method of claim 16, wherein said crosslinking agent is epichlorohydrin.

18. A method for removing iron from a patient as claimed in claim 1 comprising at least one polymer characterized by a repeat unit having the formula

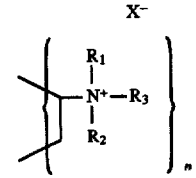

or a copolymer thereof, wherein n is an integer, each $R_1$, $R_2$ and $R_3$, independently, is H, a substituted or unsubstituted alkyl group or aminoalkyl group, or an aryl group and each $X^-$ is an exchangeable negatively charged counterion.

19. The method of claim 18 wherein said polymer is crosslinked with a crosslinking agent, wherein said agent is present in said composition from about 0.5% to about 75% by weight.

20. The method of claim 19, wherein said crosslinking agent is epichlorohydrin.

21. A method for removing iron from a patient comprising administering to said patient a therapeutically effective amount of one or more crosslinked polymers comprising
(1) a hydrophobic co-monomer and
(2) a repeat unit having the formula

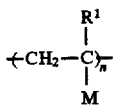

or copolymer thereof, where n is an integer; $R^1$ is H or a $C_1$–$C_{20}$ alkyl group; M is

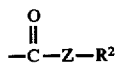

or —Z—$R_2$; Z is O, $NR^3$, S, or $(CH_2)_m$; m=0–10; $R^3$ is H or a $C_1$–$C_{20}$ alkyl group; and $R^2$ is

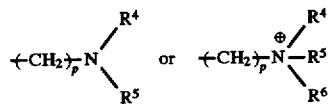

where p=0–10 and each $R^4$, $R^5$, and $R^6$, independently, is H, a $C_1$–$C_{20}$ alkyl group, or an aryl group.

22. The method of claim 21 wherein said polymer is crosslinked with a crosslinking agent wherein said crosslinking agent is present in said composition from about 0.5% to about 75% by weight.

23. The method of claim 22 wherein said crosslinking agent is epichlorohydrin.

24. A method for removing iron from a patient comprising administering to said patient a therapeutically effective amount of the reaction product of:

(a) one or more crosslinked polymers comprising a repeat unit having the formula:

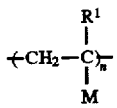

or copolymer thereof, where n is an integer; $R^1$ is H or a $C_1$–$C_{20}$ alkyl group; M is

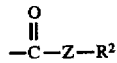

or —Z—$R^2$; Z is O, $NR^3$, S, or $(CH_2)_m$; m=0–10; $R^3$ is H or a $C_1$–$C_{20}$ alkyl group; and $R^2$ is

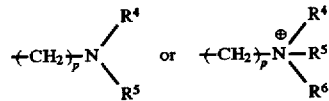

where p=0–10, and each $R^4$, $R^5$, and $R^6$, independently, is H, an alkyl group, or an aryl group.

25. The method of claim 24 wherein said polymer is crosslinked with a crosslinking agent wherein said crosslinking agent is present in said composition from about 0.5% to about 75% by weight.

26. The method of claim 25 wherein said crosslinking agent is epichlorohydrin.

27. A method for removing iron from a patient comprising administering to said patient a therapeutically effective amount of the reaction product of:

a) one or more crosslinked polymers characterized by a repeat unit selected from the group consisting of:

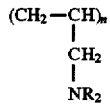

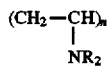

and salts and copolymers thereof, where n is an integer and each R, independently, is H or a $C_1$–$C_{20}$ alkyl group; and b) at least one alkylating agent.

28. The method of claim 27 wherein said polymer is crosslinked with a crosslinking agent wherein said crosslinking agent is present in said composition from about 0.5% to about 75% by weight.

29. The method of claim 28 wherein said crosslinking agent is epichlorohydrin.

30. A method for removing iron from a patient comprising administering to said patient a therapeutically effective amount of an amine polymer, comprising:

a) a first substituent, bound to an amine of the amine polymer, that includes a hydrophobic moiety; and b) a second substituent, bound to an amine of the amine polymer, that includes a quaternary amine-containing moiety.

31. The method of claim 30 wherein said polymer is crosslinked with a crosslinking agent wherein said crosslinking agent is present in said composition from about 0.5% to about 75% by weight.

32. The method of claim 31 wherein said crosslinking agent is epichlorohydrin.

33. A method for removing iron from a patient by ion exchange comprising administering to said patient a therapeutically effective amount an amine polymer, comprising a substituent bound to an amine of the amine polymer, the substituent including a quaternary amine-containing moiety having at least one hydrophobic substituent.

34. The method of claim 33 wherein said polymer is crosslinked with a crosslinking agent wherein said crosslinking agent is present in said composition from about 0.5% to about 75% by weight.

35. The method of claim 34 wherein said crosslinking agent is epichlorohydrin.

* * * * *

UNITED STATES PATENT AND TRADEMARK OFFICE
CERTIFICATE OF CORRECTION

PATENT NO. : 5,702,696
DATED : December 30, 1997
INVENTOR(S) : W. Harry Mandeville, III and Stephen Randall Holmes-Farley It is certified that error appears in the above-identified patent and that said Letters Patent is hereby corrected as shown below:

Column 51, Claim 12, in the formula, bottom R should be $R_2$.

Column 52, Claim 21, line 19, $-Z-R_2$ ; should be $-Z-R^2$;

Signed and Sealed this

Seventeenth Day of March, 1998

*Attest:*

BRUCE LEHMAN

*Attesting Officer*     *Commissioner of Patents and Trademarks*